US011678820B2

(12) United States Patent
Wu

(10) Patent No.: US 11,678,820 B2
(45) Date of Patent: Jun. 20, 2023

(54) METHODS AND APPARATUS FOR INFORMATION GATHERING, ERROR DETECTION AND ANALYTE CONCENTRATION DETERMINATION DURING CONTINUOUS ANALYTE SENSING

(71) Applicant: Ascensia Diabetes Care Holdings AG, Basel (CH)

(72) Inventor: Huan-Ping Wu, Granger, IN (US)

(73) Assignee: Ascensia Diabetes Care Holdings AG, Basel (CH)

( * ) Notice: Subject to any disclaimer, the term of this patent is extended or adjusted under 35 U.S.C. 154(b) by 232 days.

(21) Appl. No.: 17/014,962

(22) Filed: Sep. 8, 2020

(65) Prior Publication Data

US 2021/0068725 A1 Mar. 11, 2021

Related U.S. Application Data

(60) Provisional application No. 62/898,507, filed on Sep. 10, 2019.

(51) Int. Cl.
*G06F 17/18* (2006.01)
*A61B 5/145* (2006.01)
(Continued)

(52) U.S. Cl.
CPC ........ *A61B 5/14532* (2013.01); *A61B 5/0002* (2013.01); *A61B 5/1451* (2013.01);
(Continued)

(58) Field of Classification Search
CPC . A61B 5/14532; A61B 5/0002; A61B 5/1451; A61B 5/1495; A61B 5/6801;
(Continued)

(56) References Cited

U.S. PATENT DOCUMENTS

| | | |
|---|---|---|
| 5,792,668 A | 8/1998 | Fuller et al. |
| 8,233,958 B2 | 7/2012 | Brauker et al. |

(Continued)

FOREIGN PATENT DOCUMENTS

| | | | |
|---|---|---|---|
| CA | 3061574 A1 | 1/2019 | |
| EP | 1702561 A2 * | 9/2006 | ......... A61B 5/14532 |

(Continued)

OTHER PUBLICATIONS

International Search Report & Written Opinion of International Application No. PCT/EP2020/075174 dated Mar. 18, 2021.

(Continued)

*Primary Examiner* — Navin Natnithithadha
*Assistant Examiner* — Meghan R Kumar
(74) *Attorney, Agent, or Firm* — Erise IP, P.A.

(57) ABSTRACT

A continuous glucose monitoring (CGM) device may include a wearable portion having a sensor configured to produce glucose signals from interstitial fluid, a processor, a memory and transmitter circuitry. The memory may include a pre-determined gain function based on a point-of-interest glucose signal and glucose signals measured prior to the point-of-interest glucose signal. The memory may also include computer program code stored therein that, when executed by the processor, causes the CGM device to (a) measure and store a plurality of glucose signals using the sensor and memory; (b) for a presently-measured glucose signal, employ the plurality of previously-measured glucose signals stored in the memory and the pre-determined gain function to compute a compensated glucose value; and (c) communicate the compensated glucose value to a user of the CGM device. Numerous other embodiments are provided.

20 Claims, 21 Drawing Sheets

(51) Int. Cl.
*A61B 5/1495* (2006.01)
*A61B 5/1473* (2006.01)
*A61B 5/00* (2006.01)

(52) U.S. Cl.
CPC .......... *A61B 5/1473* (2013.01); *A61B 5/1495* (2013.01); *A61B 5/6801* (2013.01); *A61B 5/7225* (2013.01); *A61B 5/742* (2013.01); *G06F 17/18* (2013.01); *A61B 2560/0223* (2013.01)

(58) Field of Classification Search
CPC . A61B 5/7225; A61B 5/14865; A61B 5/7275; A61N 5/1473
See application file for complete search history.

(56) References Cited

U.S. PATENT DOCUMENTS

| | | | |
|---|---|---|---|
| 8,583,205 | B2 * | 11/2013 | Budiman ............ A61B 5/1495 600/347 |
| 2006/0094946 | A1 | 5/2006 | Kellogg et al. |
| 2007/0167867 | A1 | 7/2007 | Wolf |
| 2007/0270675 | A1 | 11/2007 | Kane et al. |
| 2008/0077015 | A1 | 3/2008 | Boric-Lubecke et al. |
| 2012/0283538 | A1 | 7/2012 | Rose et al. |
| 2012/0197576 | A1 | 8/2012 | Feldman |
| 2013/0071869 | A1 | 3/2013 | Wu |
| 2013/0256156 | A1 | 10/2013 | Wu et al. |
| 2014/0209460 | A1 | 7/2014 | Wu et al. |
| 2014/0273042 | A1 | 9/2014 | Saint |
| 2015/0073718 | A1 | 3/2015 | Elder et al. |
| 2015/0198555 | A1 | 7/2015 | Lee et al. |
| 2015/0351673 | A1 | 12/2015 | Vanslyke et al. |
| 2018/0275089 | A1 | 9/2018 | Huang et al. |
| 2019/0008426 | A1 | 1/2019 | Shiwaku |
| 2019/0125225 | A1 | 5/2019 | Rebec et al. |
| 2020/0268290 | A1 | 8/2020 | Zach et al. |
| 2020/0268323 | A1 | 8/2020 | Zach et al. |

FOREIGN PATENT DOCUMENTS

| | | |
|---|---|---|
| EP | 1702561 A2 | 9/2006 |
| EP | 1218532 B1 | 12/2017 |
| WO | WO2001088534 A | 11/2001 |
| WO | WO2008079435 A2 | 7/2008 |
| WO | WO-2014128638 A1 * | 8/2014 ......... A61B 5/14532 |
| WO | WO2014128638 A1 | 8/2014 |
| WO | WO2017156584 A1 | 9/2017 |

OTHER PUBLICATIONS

Nakata, S. et al.: Discrimination of Glucose from Its Interferences Using an Amperometric Sensor Based on Electrochemical Nonlinearity, Analytical Chemistry, 1998 70 (20), 4304-4308 (Year: 1998).
Invitation to Pay Fees, and attached Partial international Search Report of International Application No. PCT/EP2020/075174 dated Dec. 10, 2020.
Xu, Liang, et al.: "Optimization method for simultaneous kinetic analysis", Analytical Chem. 1996 ACS, Washington, DC, USA, vol. 68, No. 11, Jun. 1, 1996.
U.S. Appl. No. 16/782,974, filed Feb. 5, 2020, Wu et al..
U.S. Appl. No. 16/783,080, filed Feb. 5, 2020, Wu.
U.S. Appl. No. 17/014,947, filed Sep. 8, 2020, Wu.
Stein et al.: "Microscale Enzymatic Optical Biosensors Using Mass-Transport Limiting Nanofilms. 1. Fabrication and Characterization Using Glucose as a Model Analyte"; Anal Chem. Feb. 15, 2007; 79(4): 1339-1348. DOI: 10.1021/ac061414z; https://www.ncbi.nlm.nih.gov/pmc/articles/PMC2518633/.
Haxha. et al.: "Optical Based Noninvasive Glucose Monitoring Sensor Prototype"; University of Bedfordshire, Luton , U.K.; IEEE Photonics Journal: vol. 8, No. 6, Dec. 2016. DOI: 10.1109/JPHOT.2016.2616491 1943-0655.
Parkes et al.: "A New Consensus Error Grid to Evaluate the Clinical Significance of Inaccuracies in the Measurement of Blood Glucose"; Diabetes Care, vol. 23, No. 8, Aug. 2000.
Nakata et al., "Discrimination of Glucose from Its Interferences Using an Amperometric Sensor Based on Electrochemical Nonlinearity", Analytical Chemistry, American Chemical Society, US, vol. 70, No. 20, Oct. 15, 1998, pp. 4304-4308, XP000789048, ISSN: 0003-2700, DOI: 10.1021/AC980442H.
Bond et al., "An integrated instrumental and theoretical approach to quantitative electrode kinetic studies based on large amplitude Fourier transformed a.c. volatammetry: A mini review", Electrochemistry Communications, Elsevier, Amsterdam, NL, vol. 57, May 8, 2015, pp. 78-83, XP029212452, ISSN: 1388-2481, DOI: 10.1016/J.Elecom.2015.04.017.
Nakata et al., "Experimental Demonstration and Simulation of Electrochemical Non-linear Reponses to Glucose and Its Interferents with an Amperometric Senso", Analyst, London, GB, vol. 124, No. 8, Aug. 1, 1999, pp. 1175-1179, XP001039882, DOI: 10.1039/A903187A.

* cited by examiner

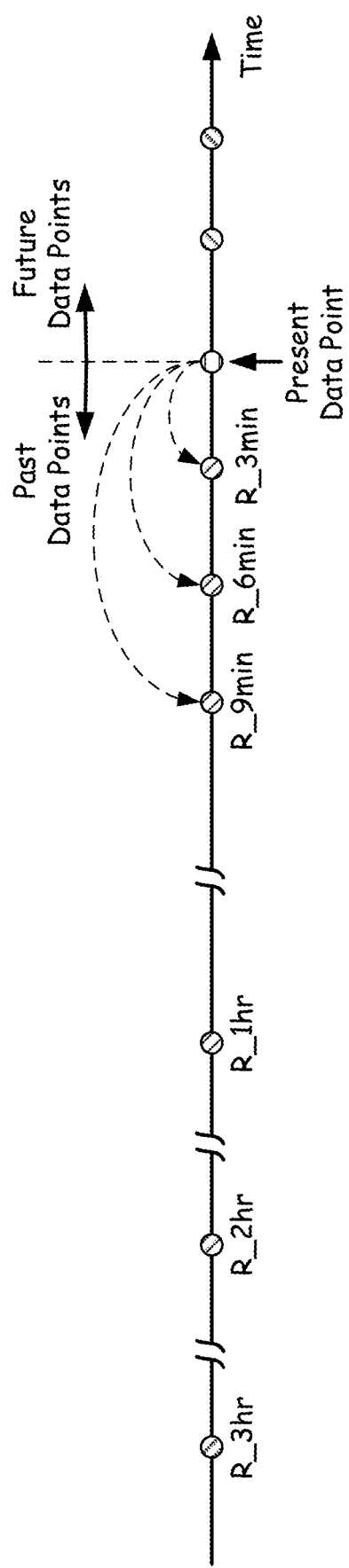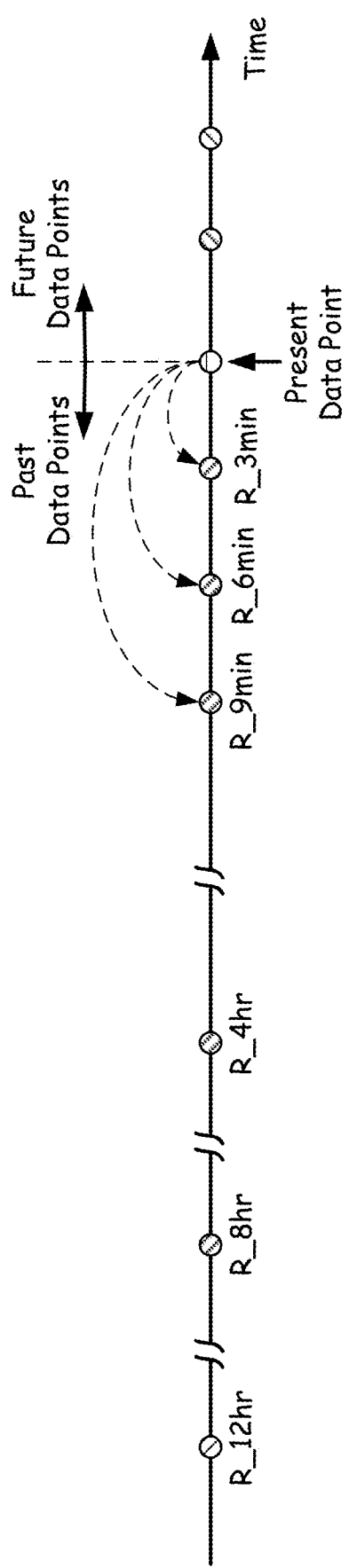

| GAIN FUNCTION 1 (3-20 HOURS) |
|---|
| Gain Function 1 = 3.091118 + 1.471262*w27min - 0.984106*w2h - 2.665682*b3min - 2.254352*b18min + 2.314656*b1h - 0.0149674*w6mG - 0.0227495*w24mG + 1.117723*w27mSS1 + 0.951549*w3hSS1 + 0.0020214*w3hGSS1 + 0.536988*w3m2h - 0.97541*w9m2h + 0.326197*w15m1h + 0.699317*w24m2h - 0.397502*w27m2h + 0.0287526*b3mG - 0.01240012*b6mG - 0.43543*b3hSS1 - 0.0025204*b30mGSS1 - 0.841776*w27mb6mSS1 - 1.268666*w3hb9mSS1 ... |

FIG. 4A

| GAIN FUNCTION 2 (12-45 HOURS) |
|---|
| Gain Function 2 = 6.333784 + 2.7006532*w9min - 0.4503101*b1h - 0.0004858*w9mGSS1 + 9.35e-5*w12hGSS1 + 0.0930561*w3m3h - 0.0721993*w3m12h + 0.292186*w9m1h - 0.2503538*w12m2h - 0.231265*w21m2h + 0.508004*w24m2h - 0.2291636*w30m1h - 0.0584004*w30m3h + 0.0409812*w30m4h - 0.0041765*b6mG + 0.0039682*b12hG - 0.1346056*b6hSS1 + 0.0010892*b1hGSS1 + 0.0009736*b10hGSS1 + 0.1471952*w8hb4hSS1 - 0.0364746*w12hb4hSS1 ... |

FIG. 4B

| GAIN FUNCTION 3 (40-167 HOURS) |
|---|
| Gain Function 3 = 0.979878 - 0.637773*w9min + 0.0001337*w2hGSS1 + 0.0001573*w12hGSS1 + 0.167157*w3m3h - 0.325834*w3m12h + 0.311399*w6m12h + 0.378304*w12m1h - 0.308914*w12m3h - 0.022367*w18m10h - 0.377033*w27m1h + 0.167712*w27m3h - 0.390158*b15mSS1 + 0.356742*b8hSS1 - 0.0008352*b9mGSS1 + 0.0008576*b4hGSS1 - 0.204995*w3mb2h - 0.59261*w6mb1h + 0.0020452*Gw12hb12h - 0.296086*w12hb12mSS1 + 0.289866*w12hb12hSS1 ... |

FIG. 4C

GAIN FUNCTION 1 SPPs AND CROSS TERMS $Gain_i = BGM_{cal-i}/(Iw-Ib)_{cal-i}$, at $i$ in-situ calibration point where $i = 1, 2, \ldots 10$, etc.

$S/S1 = Gain_i/Gain_1$, the ratio of an individual $Gain_i$ to $Gain_1 = BGM_{cal-1}/(Iw-Ib)_{cal-1}$ $G_{raw} = 0.85*(Iw-Ib)_t*Gain_i$, if $Gain_i > 12$; elseif $Gain_i > 8$, $0.9*(Iw-Ib)_t*Gain_i$; else $(Iw-Ib)_t*Gain_i$ $w27min = (Iw-Ib)_t/(Iw-Ib)_{t-27min}$, ratio of $Iw-Ib$ at time $t$ to $Iw-Ib$ at time of $t-27min$ $w2h = (Iw-Ib)_t/(Iw-Ib)_{t-2hour}$, ratio of $Iw-Ib$ at time $t$ to $Iw-Ib$ at time of $t-2hour$ $b3min = Ib_t/Ib_{t-3min}$, ratio of $Ib$ at time $t$ to $Ib$ at time of $t-3min$ $b18min = Ib_t/Ib_{t-18min}$ $b1h = Ib_t/Ib_{t-1hour}$ $w6mG = G_{raw}*(Iw-Ib)_t/(Iw-Ib)_{t-6min}$ $w24mG = G_{raw}*(Iw-Ib)_t/(Iw-Ib)_{t-24min}$ $w27mSS1 = (S/S1)*(Iw-Ib)_t/(Iw-Ib)_{t-27min}$ $w3hSS1 = (S/S1)*(Iw-Ib)_t/(Iw-Ib)_{t-3hour}$ $w3hGSS1 = G_{raw}*(S/S1)*(Iw-Ib)_t/(Iw-Ib)_{t-3hour}$ $w3m2h = w\_3min/w\_2h = [(Iw-Ib)_t/(Iw-Ib)_{t-3min}]/[(Iw-Ib)_t/(Iw-Ib)_{t-2hour}] = (Iw-Ib)_{t-2hour}/(Iw-Ib)_{t-3min}$ $w9m2h = w\_9min/w\_2h = [(Iw-Ib)_t/(Iw-Ib)_{t-9min}]/[(Iw-Ib)_t/(Iw-Ib)_{t-2hour}] = (Iw-Ib)_{t-2hour}/(Iw-Ib)_{t-9min}$ $w15m1h = w\_15min/w\_1h = [(Iw-Ib)_t/(Iw-Ib)_{t-15min}]/[(Iw-Ib)_t/(Iw-Ib)_{t-1hour}] = (Iw-Ib)_{t-1hour}/(Iw-Ib)_{t-15min}$ $w24m2h = w\_24min/w\_2h = [(Iw-Ib)_t/(Iw-Ib)_{t-24min}]/[(Iw-Ib)_t/(Iw-Ib)_{t-2hour}] = (Iw-Ib)_{t-2hour}/(Iw-Ib)_{t-24min}$ $w27m2h = w\_27min/w\_2h = [(Iw-Ib)_t/(Iw-Ib)_{t-27min}]/[(Iw-Ib)_t/(Iw-Ib)_{t-2hour}] = (Iw-Ib)_{t-2hour}/(Iw-Ib)_{t-27min}$ $b3mG = G_{raw}*Ib_t/Ib_{t-3min}$ $b6mG = G_{raw}*Ib_t/Ib_{t-6min}$ $b3hSS1 = (S/S1)*Ib_t/Ib_{t-3hour}$ $b30mGSS1 = G_{raw}*(S/S1)*Ib_t/Ib_{t-30min}$ $w27mb6mSS1 = (S/S1)*w\_27min/b\_6min = (S/S1)*[(Iw-Ib)_t/(Iw-Ib)_{t-27min}]/[Ib_t/Ib_{t-6min}]$ $w3hb9mSS1 = (S/S1)*w\_3h/b\_9min = (S/S1)*[(Iw-Ib)_t/(Iw-Ib)_{t-3hour}]/[Ib_t/Ib_{t-9min}]$

FIG. 4D

GAIN FUNCTION 2 SPPs AND CROSS TERMS $Gain_i = BGM_{cal-i}/(Iw-Ib)_{cal-i}$, at i in-situ calibration point where i = 1, 2, .....10, etc.

$S/S1 = Gain_i/Gain_1$, the ratio of an individual $Gain_i$ to $Gain1 = BGM_{cal-1}/(Iw-Ib)_{cal-1}$ $G_{raw} = 0.85*(Iw-Ib)_t*Gain_i$, if $Gain_i>12$; elseif $Gain_i>8$, $0.9*(Iw-Ib)_t*Gain_i$; else $(Iw-Ib)_t*Gain_i$ $w9min = (Iw-Ib)_t/(Iw-Ib)_{t-9min}$, ratio of Iw-Ib at time t to Iw-Ib at time of t-9min $b1h = Ib_t/Ib_{t-1hour}$, ratio of Ib at time t to Ib at time of t-1hour $w9mGSS1 = G_{raw}*(S/S1)*(Iw-Ib)_t/(Iw-Ib)_{t-9min}$ $w12hGSS1 = G_{raw}*(S/S1)*(Iw-Ib)_t/(Iw-Ib)_{t-12hour}$ $w3m3h = w\_3min/w\_3h = [(Iw-Ib)_t/(Iw-Ib)_{t-3min}]/[(Iw-Ib)_t/(Iw-Ib)_{t-3hour}] = (Iw-Ib)_{t-3hour}/(Iw-Ib)_{t-3min}$ $w3m12h = w\_3min/w\_12h = [(Iw-Ib)_t/(Iw-Ib)_{t-3min}]/[(Iw-Ib)_t/(Iw-Ib)_{t-12hour}] = (Iw-Ib)_{t-12hour}/(Iw-Ib)_{t-3min}$ $w9m1h = w\_9min/w\_1h = [(Iw-Ib)_t/(Iw-Ib)_{t-9min}]/[(Iw-Ib)_t/(Iw-Ib)_{t-1hour}] = (Iw-Ib)_{t-1hour}/(Iw-Ib)_{t-9min}$ $w12m2h = w\_12min/w\_2h = [(Iw-Ib)_t/(Iw-Ib)_{t-12min}]/[(Iw-Ib)_t/(Iw-Ib)_{t-2hour}] = (Iw-Ib)_{t-2hour}/(Iw-Ib)_{t-12min}$ $w21m2h = w\_21min/w\_2h = [(Iw-Ib)_t/(Iw-Ib)_{t-21min}]/[(Iw-Ib)_t/(Iw-Ib)_{t-2hour}] = (Iw-Ib)_{t-2hour}/(Iw-Ib)_{t-21min}$ $w24m2h = w\_24min/w\_2h = [(Iw-Ib)_t/(Iw-Ib)_{t-24min}]/[(Iw-Ib)_t/(Iw-Ib)_{t-2hour}] = (Iw-Ib)_{t-2hour}/(Iw-Ib)_{t-24min}$ $w30m1h = w\_30min/w\_1h = [(Iw-Ib)_t/(Iw-Ib)_{t-30min}]/[(Iw-Ib)_t/(Iw-Ib)_{t-1hour}] = (Iw-Ib)_{t-1hour}/(Iw-Ib)_{t-30min}$ $w30m3h = w\_30min/w\_3h = [(Iw-Ib)_t/(Iw-Ib)_{t-30min}]/[(Iw-Ib)_t/(Iw-Ib)_{t-3hour}] = (Iw-Ib)_{t-3hour}/(Iw-Ib)_{t-30min}$ $w30m4h = w\_30min/w\_4h = [(Iw-Ib)_t/(Iw-Ib)_{t-30min}]/[(Iw-Ib)_t/(Iw-Ib)_{t-4hour}] = (Iw-Ib)_{t-4hour}/(Iw-Ib)_{t-30min}$ $b6mG = G_{raw}*Ib_t/Ib_{t-6min}$ $b12hG = G_{raw}*Ib_t/Ib_{t-12hour}$ $b6hSS1 = (S/S1)*Ib_t/Ib_{t-6hour}$ $b1hGSS1 = G_{raw}*(S/S1)*Ib_t/Ib_{t-1hour}$ $b10hGSS1 = G_{raw}*(S/S1)*Ib_t/Ib_{t-10hour}$ $w8hb4hSS1 = (S/S1)*w\_8h/b\_4h = (S/S1)*[(Iw-Ib)_t/(Iw-Ib)_{t-8hour}]/[Ib_t/Ib_{t-4hour}]$ $w12hb4hSS1 = (S/S1)*w\_12h/b\_4h = (S/S1)*[(Iw-Ib)_t/(Iw-Ib)_{t-12hour}]/[Ib_t/Ib_{t-4hour}]$

FIG. 4E

GAIN FUNCTION 3 SPPs AND CROSS TERMS $Gain_i = BGM_{cal-i}/(Iw-Ib)_{cal-i}$, at i in-situ calibration point where i = 1, 2, .....10, etc.

$S/S1 = Gain_i/Gain_1$, the ratio of an individual $Gain_i$ to $Gain_1 = BGM_{cal-1}/(Iw-Ib)_{cal-1}$ $G_{raw} = 0.85*(Iw-Ib)t*Gain_i$, if $Gain_i>12$; elseif $Gain_i>8$, $0.9*(Iw-Ib)t*Gain_i$; else $(Iw-Ib)t*Gain_i$ $w9min = (Iw-Ib)_t/(Iw-Ib)_{t-9min}$, ratio of Iw-Ib at time t to Iw-Ib at time of t-9min $w2hGSS1 = G_{raw}*(S/S1)*(Iw-Ib)_t/(Iw-Ib)_{t-2hour}$ $w12hGSS1 = G_{raw}*(S/S1)*(Iw-Ib)_t/(Iw-Ib)_{t-12hour}$ $w3m3h = w\_3min/w\_3h = [(Iw-Ib)_t/(Iw-Ib)_{t-3min}]/[(Iw-Ib)_t/(Iw-Ib)_{t-3hour}] = (Iw-Ib)_{t-3hour}/(Iw-Ib)_{t-3min}$ $w3m12h = w\_3min/w\_12h = [(Iw-Ib)_t/(Iw-Ib)_{t-3min}]/[(Iw-Ib)_t/(Iw-Ib)_{t-12hour}] = (Iw-Ib)_{t-12hour}/(Iw-Ib)_{t-3min}$ $w6m12h = w\_6min/w\_12h = [(Iw-Ib)_t/(Iw-Ib)_{t-6min}]/[(Iw-Ib)_t/(Iw-Ib)_{t-12hour}] = (Iw-Ib)_{t-12hour}/(Iw-Ib)_{t-6min}$ $w12m1h = w\_12min/w\_1h = [(Iw-Ib)_t/(Iw-Ib)_{t-12min}]/[(Iw-Ib)_t/(Iw-Ib)_{t-1hour}] = (Iw-Ib)_{t-1hour}/(Iw-Ib)_{t-12min}$ $w12m3h = w\_12min/w\_3h = [(Iw-Ib)_t/(Iw-Ib)_{t-12min}]/[(Iw-Ib)_t/(Iw-Ib)_{t-3hour}] = (Iw-Ib)_{t-3hour}/(Iw-Ib)_{t-12min}$ $w18m10h = w\_18min/w\_10h = [(Iw-Ib)_t/(Iw-Ib)_{t-18min}]/[(Iw-Ib)_t/(Iw-Ib)_{t-10hour}] = (Iw-Ib)_{t-10hour}/(Iw-Ib)_{t-18min}$ $w27m1h = w\_27min/w\_1h = [(Iw-Ib)_t/(Iw-Ib)_{t-27min}]/[(Iw-Ib)_t/(Iw-Ib)_{t-1hour}] = (Iw-Ib)_{t-1hour}/(Iw-Ib)_{t-27min}$ $w27m3h = w\_27min/w\_3h = [(Iw-Ib)_t/(Iw-Ib)_{t-27min}]/[(Iw-Ib)_t/(Iw-Ib)_{t-3hour}] = (Iw-Ib)_{t-3hour}/(Iw-Ib)_{t-27min}$ $b15mSS1 = (S/S1)*Ib_t/Ib_{t-15min}$ $b8hSS1 = (S/S1)*Ib_t/Ib_{t-8hour}$ $b9mGSS1 = G_{raw}*(S/S1)*Ib_t/Ib_{t-9min}$ $b4hGSS1 = G_{raw}*(S/S1)*Ib_t/Ib_{t-4hour}$ $w3mb2h = w\_3min/b\_2h = [(Iw-Ib)_t/(Iw-Ib)_{t-3min}]/[Ib_t/Ib_{t-2hour}]$ $w6mb1h = w\_6min/b\_1h = [(Iw-Ib)_t/(Iw-Ib)_{t-6min}]/[Ib_t/Ib_{t-1hour}]$ $Gw12hb12h = G_{raw}*w\_12h/b\_12h = G_{raw}*[(Iw-Ib)_t/(Iw-Ib)_{t-12hour}]/[Ib_t/Ib_{t-12hour}]$ $w12hb12mSS1 = (S/S1)*w\_12h/b\_12min = (S/S1)*[(Iw-Ib)_t/(Iw-Ib)_{t-12hour}]/[Ib_t/Ib_{t-12min}]$ $w12hb12hSS1 = (S/S1)*w\_12h/b\_12h = (S/S1)*[(Iw-Ib)_t/(Iw-Ib)_{t-12hour}]/[Ib_t/Ib_{t-12hour}]$

FIG. 4F

METHODS AND APPARATUS FOR INFORMATION GATHERING, ERROR DETECTION AND ANALYTE CONCENTRATION DETERMINATION DURING CONTINUOUS ANALYTE SENSING

RELATED APPLICATION

The present application claims priority to and the benefit of U.S. Provisional Patent Application No. 62/898,507, filed Sep. 10, 2019 and titled "METHODS AND APPARATUS FOR INFORMATION GATHERING, ERROR DETECTION AND ANALYTE CONCENTRATION DETERMINATION DURING CONTINUOUS ANALYTE SENSING," which is hereby incorporated by reference herein in its entirety for all purposes.

FIELD

The present disclosure relates generally to determining analyte concentration in an analyte-containing fluid using continuous analyte sensing.

BACKGROUND

Continuous analyte sensing in an in-vivo and/or in-vitro sample, such as continuous glucose monitoring (CGM), has become a routine sensing operation, particularly in diabetes care. By providing real-time glucose concentrations, therapeutic/clinical actions may be applied timelier and the glycaemic condition may be better controlled.

During a CGM operation, a biosensor is typically inserted subcutaneously and continuously operated in an environment surrounded by tissues and interstitial fluid (ISF). The biosensor may be continuously operated at a constant potential against a reference electrode, such as an Ag/AgCl electrode, or a combined reference-counter electrode. The biosensor may also be operated with two working electrodes where one is dedicated to measuring a point-of-interest analyte, such as glucose, by a glucose specific enzyme such as glucose oxidase. The other electrode is dedicated to measuring the background signals that result from interference species such as uric acid, acetaminophen or the like. In this dual electrode operation scheme, the interference signal may be constantly subtracted from the main signal of the point-of-interest analyte by either simple subtraction or another algorithmic method.

Optical sensors may also be used for continuous glucose monitoring, employing fluorescence, absorbance, reflectance, and/or the like. For instance, an optical oxygen sensor relying on fluorescence or quenching of fluorescence has been employed to indirectly measure glucose by measuring the oxygen concentration in ISF, which has an inverse relationship to the glucose concentration. (See, for example, Stein et. al, "Microscale Enzymatic Optical Biosensors using Mass-Transport Limiting Nanofilms. 1. Fabrication and Characterization using Glucose as a Model Analyte," Anal Chem, Author Manuscript, 2008 www.ncbi.nlm/nih-.gov/pmc/articles/PMC2518633/)

To measure the concentration of an analyte in a sample using an analytical method, reference concentrations may be employed to determine the accuracy of the analytical method. For biosensors deployed subcutaneously and exposed to interstitial fluid, the glucose signals by definition are responsive to ISF glucose. However, determining ISF glucose concentration directly is difficult as ISF samples are not readily available for reference ISF glucose measurements. Furthermore, the related therapeutic action based on glycaemic status is more dependent on the capillary glucose which is delivered to cells through the capillary system.

As is known, ISF glucose lags behind capillary glucose by about 5 to 15 minutes, depending on whether the biological body system is fasting or is at a glucose changing stage. As such, ISF glucose may only serve as an indicator for capillary glucose given the time lag; and providing an accurate prediction of capillary glucose using CGM biosensors is a challenge. In addition, the signal noise due to sensitivity changes over time relative to system calibration (in-situ calibration or factory calibration), tissue effects on the biosensor membrane, and other known factors, render the ISF glucose timing profile relative to capillary glucose less defined.

One conventional method of reducing ISF glucose lag and thus increasing CGM accuracy is through filtering. Another method is the so-called lag-compensation in which estimated glucose values are compared to measured glucose values and used to compensate for lag. However, because there is error associated with the determination of ISF glucose due to the factors mentioned above, the filtering method or the lag-compensation method may prove to be less meaningful.

Improved CGM methods and apparatus are desired.

SUMMARY

In some embodiments, a method of making a continuous glucose monitoring (CGM) device includes (1) creating a gain function based on a plurality of sensor progression parameters of glucose signals measured by a CGM sensor, each sensor progression parameter based on a point-of-interest glucose signal and a glucose signal measured prior to the point-of-interest glucose signal; (2) providing a CGM device including a sensor, a memory and a processor; (3) storing the gain function in the memory of the CGM device; (4) storing computer program code in the memory of the CGM device that, when executed by the processor, causes the CGM device to (a) measure and store a plurality of glucose signals using the sensor and memory of the CGM device; (b) for a presently-measured glucose signal, compute a plurality of sensor progression parameters based on the presently-measured glucose signal and a plurality of previously-measured glucose signals stored in the memory; (c) employ the plurality of sensor progression parameters and the stored gain function to compute a compensated glucose value; and (d) communicate the compensated glucose value to a user of the CGM device.

In some embodiments, a continuous glucose monitoring (CGM) device includes a wearable portion having a sensor configured to produce glucose signals from interstitial fluid; a processor; a memory coupled to the processor; and transmitter circuitry coupled to the processor. The memory includes a gain function based on a plurality of sensor progression parameters of glucose signals, each sensor progression parameter based on a point-of-interest glucose signal and a glucose signal measured prior to the point-of-interest glucose signal. The memory includes computer program code stored therein that, when executed by the processor, causes the CGM device to (a) measure and store a plurality of glucose signals using the sensor and memory of the wearable portion; (b) for a presently-measured glucose signal, compute a plurality of sensor progression parameters based on the presently-measured glucose signal and a plurality of previously-measured glucose signals stored in the memory; (c) employ the plurality of sensor progression parameters and the stored gain function to compute a compensated glucose value; and (d) communicate the compensated glucose value to a user of the CGM device.

In some embodiments, a continuous glucose monitoring (CGM) device includes a wearable portion having a sensor configured to produce glucose signals from interstitial fluid; current sensing circuitry coupled to the sensor and configured to measure the glucose signals produced by the sensor; and transmitter circuitry configured to transmit the measured glucose signals. The CGM device also includes a portable user device having a memory, a processor, and receiver circuitry configured to receive glucose signals from the wearable portion. The memory includes a gain function based on a plurality of sensor progression parameters of glucose signals, each sensor progression parameter based on a point-of-interest glucose signal and a glucose signal measured prior to the point-of-interest glucose signal. The memory includes computer program code stored therein that, when executed by the processor, causes the CGM device to (a) obtain and store a plurality of glucose signals using the sensor of the wearable portion and the memory of the portable user device; (b) for a presently-measured glucose signal, compute a plurality of sensor progression parameters based on the presently-measured glucose signal and a plurality of previously-measured glucose signals stored in the memory; (c) employ the plurality of sensor progression parameters and the stored gain function to compute a compensated glucose value; and (d) communicate the compensated glucose value to a user of the CGM device.

In some embodiments, a method of compensating for errors during continuous glucose monitoring (CGM) measurements includes (a) providing a CGM device including a sensor, a memory and a processor, the CGM device having a gain function stored in the memory, the gain function based on a plurality of sensor progression parameters of glucose signals, each sensor progression parameter based on a point-of-interest glucose signal and a glucose signal measured prior to the point-of-interest glucose signal; (b) measuring and storing a plurality of glucose signals using the sensor and memory; (c) for a presently-measured glucose signal, computing a plurality of sensor progression parameters based on the presently-measured glucose signal and a plurality of previously-measured glucose signals stored in the memory; (d) employing the plurality of sensor progression parameters and the stored gain function to compute a compensated glucose value; and (e) communicating the compensated glucose value to a user of the CGM device.

In some embodiments, a method of determining analyte concentrations during continuous monitoring measurements includes (a) inserting a biosensor subcutaneously into a subject, the biosensor including a counter electrode, a reference electrode and a working electrode having a chemical composition configured to oxidize a point-of-interest analyte; (b) applying a constant voltage to the working electrode having the chemical composition so as to generate a continuous current flow from the working electrode; (c) sensing and storing working electrode current signals from the working electrode into a memory; (d) gathering a point-of-interest working electrode current signal and a portion of the working electrode current signals stored in the memory which were measured prior to the point-of-interest working electrode current signal; (e) generating a gain function value from a predetermined gain function employing the point-of-interest working electrode current signal and the portion of the working electrode current signals gathered from the memory; (f) modifying a system gain using the gain function value generated from the predetermined gain function; and (g) determining an analyte concentration for the point-of-interest working electrode current signal based on the modified system gain and the point-of-interest working electrode current signal.

In some embodiments, a continuous analyte monitoring (CAM) device is provided that includes a wearable portion having a biosensor configured to be subcutaneously inserted into a subject, the biosensor including a counter electrode, a reference electrode and a working electrode having a chemical composition configured to oxidize a point-of-interest analyte and to produce analyte signals from interstitial fluid; a processor; a memory coupled to the processor; and transmitter circuitry coupled to the processor. The memory includes a predetermined gain function based on a point-of-interest analyte signal and analyte signals measured prior to the point-of-interest analyte signal. The memory includes computer program code stored therein that, when executed by the processor, causes the CAM device to (a) apply a constant voltage to the working electrode having the chemical composition so as to generate a continuous current flow from the working electrode; (b) sense and store working electrode current signals from the working electrode into the memory; (c) gather a point-of-interest working electrode current signal and a portion of the working electrode current signals stored in the memory which were measured prior to the point-of-interest working electrode current signal; (d) generate a gain function value from the gain function employing the point-of-interest working electrode current signal and the portion of the working electrode current signals gathered from the memory; (e) modify a system gain using the gain function value generated from the predetermined gain function; and (f) determine an analyte concentration for the point-of-interest working electrode current signal based on the modified system gain and the point-of-interest working electrode current signal.

In some embodiments, a method of making a continuous analyte monitoring device includes (a) operatively coupling an analyte sensor with a host for use during a continuous analyte monitoring process; (b) recording analyte signals continuously during the continuous analyte monitoring process; (c) recording reference analyte concentrations during the continuous analyte monitoring process; (d) establishing a data pairing between analyte signals and reference analyte concentrations; (e) calculating relative analyte error referenced against reference analyte concentration; (f) gathering sensor progression information and calculating sensor progression parameters by referencing point-of-interest analyte data points to previously-measured analyte data points; (g) conducting statistical analysis by setting at least one of relative analyte error referenced against reference analyte concentration and relative gain error referenced against reference gain as a target for the statistical analysis and sensor progression parameters as input variables so as to obtain a gain function; and (h) recording the gain function including selected sensor progression parameters and their weighted coefficients as a factory calibration component for storage in a continuous analyte monitoring device.

Other features, aspects, and advantages of embodiments in accordance with the present disclosure will become more fully apparent from the following detailed description, the subjoined claims, and the accompanying drawings by illustrating a number of example embodiments and implementations. Various embodiments in accordance with the present disclosure may also be capable of other and different applications, and its several details may be modified in various respects, all without departing from the spirit and scope of the claims. Accordingly, the drawings and descriptions are to

BRIEF DESCRIPTION OF THE DRAWINGS

Figure 1C:
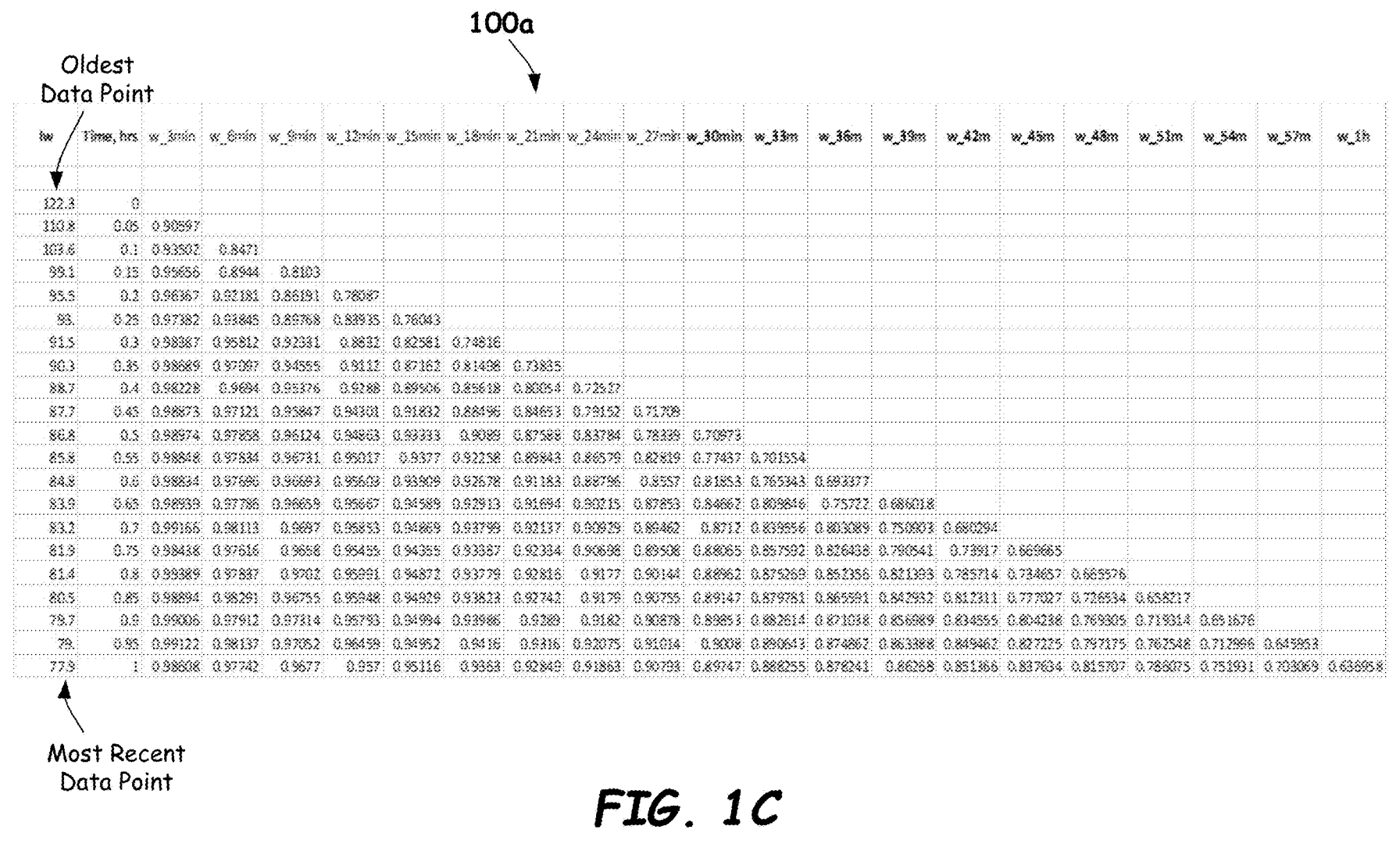
Figure 1D:
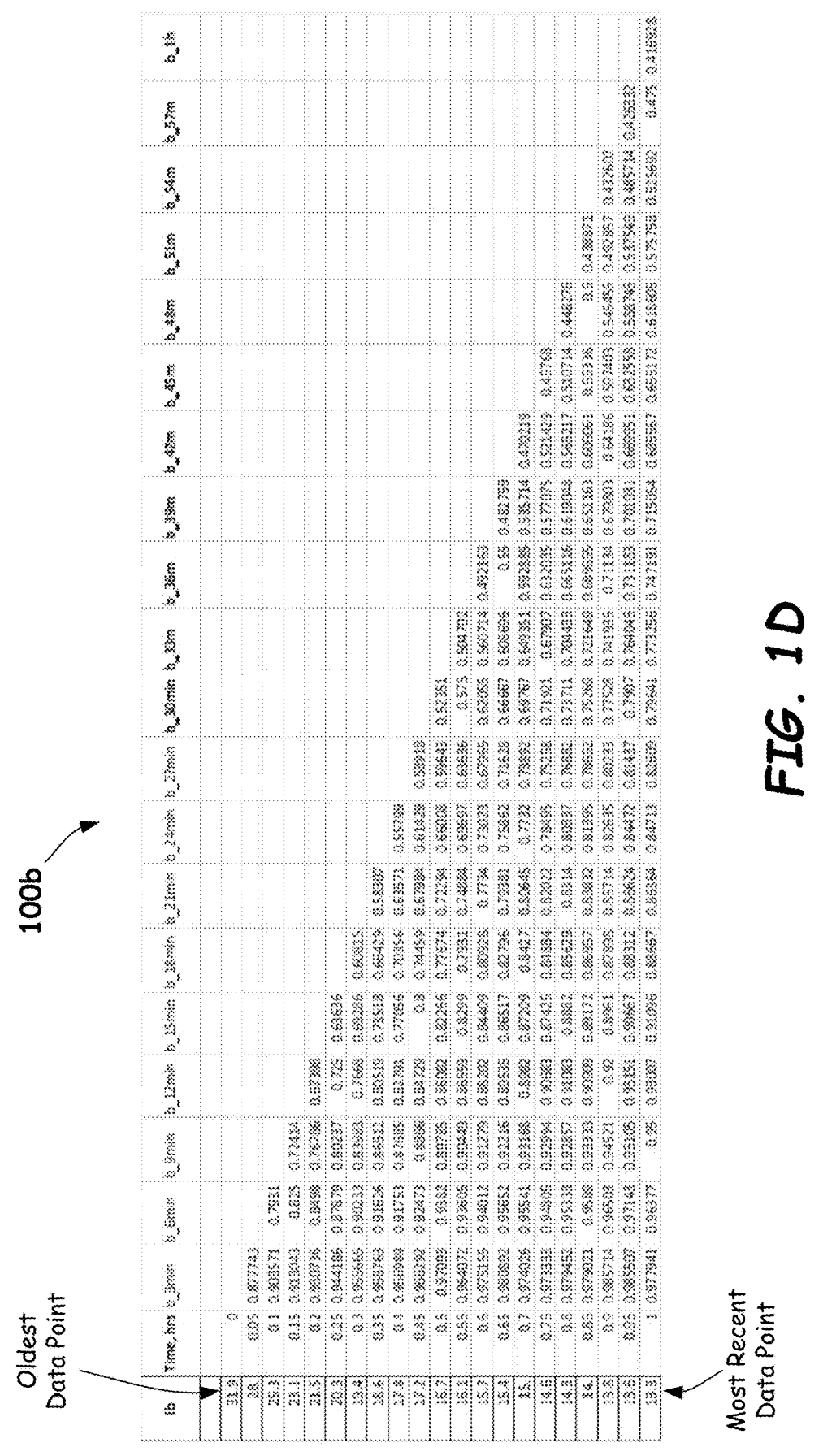
Figure 1E:
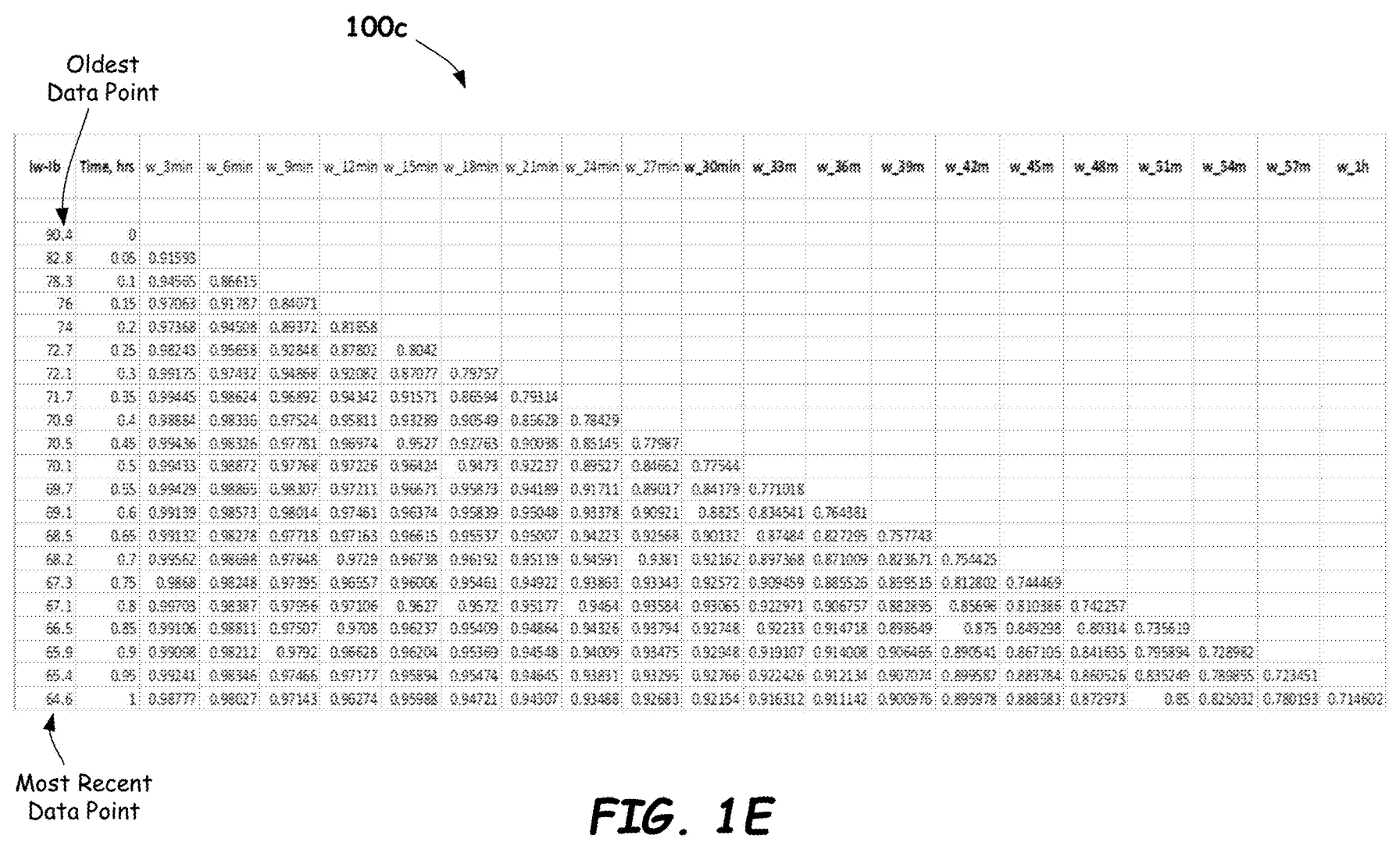

FIG. 1A illustrates referencing a present data point to past data points in a collection of glucose signals taken over a three-hour period, and use of the collected glucose signals to compute sensor progression parameters such as ratios in accordance with embodiments described herein.

FIG. 1B illustrates referencing a present data point to past data points in a collection of glucose signals taken over a twelve-hour period, and use of the collected glucose signals to compute sensor progression parameters such as ratios in accordance with embodiments described herein.

FIGS. 1C, 1D and 1E illustrate tables of example ratios for working electrode current Iw, background electrode current Ib, and Iw−Ib current differential, respectively, of a CGM sensor using prior data points measured up to 1 hour before the last data point (taken at Time=1 hour), in accordance with embodiments provided herein.

FIGS. 4A, 4B and 4C illustrate example gain functions for segments of FIG. 2 (referred to as Gain Function 1, Gain Function 2 and Gain Function 3 in FIGS. 4A-C) in accordance with embodiments described herein.

FIGS. 4D, 4E and 4F are listings of definitions of ratios and cross terms for the Gain Functions of FIGS. 4A, 4B and 4C, respectively, in accordance with embodiments described herein.

DETAILED DESCRIPTION

Overview

Figure 1F:
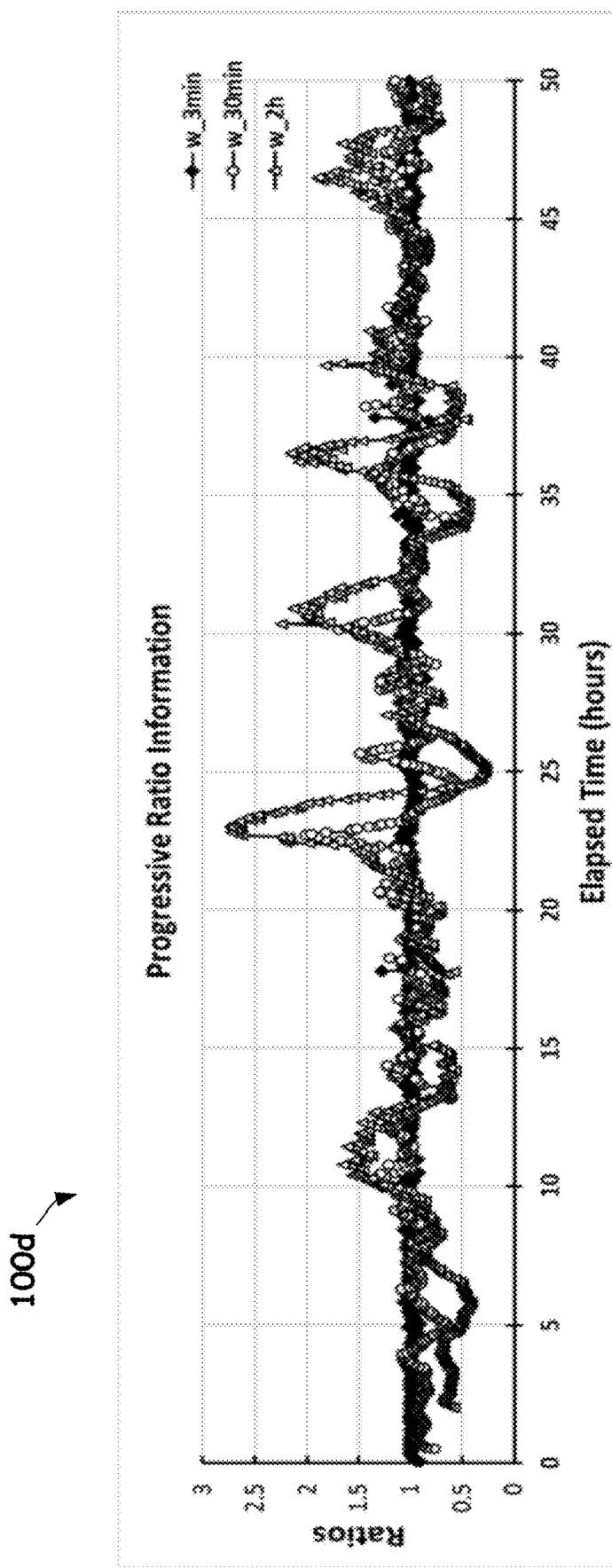
FIG. 1F illustrates a graph of example ratios versus elapsed time for working electrode current signals taken over a period of 50 hours, in accordance with embodiments provided herein.

In order to more closely monitor a person's glucose level and detect shifts in glucose level, methods and apparatus for continuous glucose monitoring (CGM) have been developed. While CGM systems generate glucose signals "continuously" during operation, such as continuous electrochemical and/or optical signals, measurements of the generated glucose signals are typically performed every few minutes, rather than being truly continuous. CGM systems, which have an implantable portion and a non-implantable portion, may be worn for several days before being removed and replaced. CGM systems may include a sensor portion that is inserted so as to be located under the skin, and a non-implanted processing portion that is adhered to the outer surface of the skin, for example the abdomen, or the back of the upper arm. Unlike a blood glucose monitoring (BGM) system that measures glucose concentration in blood, CGM systems measure glucose concentration in interstitial fluid or in samples of non-direct capillary blood.

CGM systems may provide frequent measurements of a person's glucose levels without the need for each such measurement to be accompanied by the drawing of a blood sample, such as by finger sticks. CGM systems may still employ occasional finger sticks and the use of a BGM system, such as the Contour NEXT One® by Ascensia Diabetes Care AG of Basel Switzerland, for calibrating the CGM systems.

As stated previously, during CGM, a biosensor may be continuously operated at a constant potential against a reference electrode or a combined reference-counter electrode. No method equivalent to the gated amperometry used in the field of BGM has been employed during CGM because the potential pulsing for each data point may destabilize the resultant glucose signals, leading to poor signal quality. Thus, there is a lack of meaningful information readily available to assist the glucose determination through algorithmic methods during CGM.

Within the field of BGM testing, the gated amperometry methods described in US Patent Publication No. 2013/0256156, titled "Gated Amperometry Methods," apply a bias voltage to a test strip, and a group of signals/data points are measured in response to the applied bias for the final analyte determination. In the segmented signal processing methods of optical sensors and electrochemical sensors described in US Patent Publication No. 2013/0071869, titled "Analysis Compensation Including Segmented Signals," the data points within a single process are used together to provide information for end-point analyte determination. These patent publications describe discrete tests in transient processes where one analyte determination is independent of all other analyte determinations. Thus, the group of signals/data points from a single sensor testing is used only to provide a single glucose measurement/analyte determination for a test strip/cartridge. Each subsequent glucose/analyte measurement relies on a new group of data points (and a new test strip/cartridge).

In contrast, during a continuous glucose monitoring process, in accordance with embodiments described herein, each measured signal/data point is its own end-point for analyte determination in a data continuum, but is also related to its adjacent data points in short term and/or long-term relationships. In accordance with embodiments provided herein, because of the continuous nature of CGM, prior signals/data points may contain information relevant to subsequently measured signals/data points. That is, each data point may be related to its adjacent (e.g., previous) data points, or even data points taken much earlier in time. The relationships of the present (point-of-interest) data point to many of the previously-measured data points in a continuum have been found to contain sensor error and/or status information (referred to herein as "sensor progression information"). In some embodiments, prior data points may become a source of information suggestive of sensor error source or sensor status. Parameters relating a present data point, or a point-of-interest data point, to previously-measured data points are referred to herein as sensor progression parameters (SPPs).

As described herein, sensor progression parameters in CGM or other continuous analyte monitoring methods may be determined by referencing a present analyte signal to previously-measured analyte signals in a data continuum in the forms of ratios, differences, relative differences and/or the like. According to one or more embodiments described herein, a method is thus provided for information gathering for CGM glucose concentration determinations and/or error compensation. In some embodiments, the method may include employing previously-measured glucose signals from a CGM sensor with a present, point-of-interest CGM glucose signal to generate a gain function value. The gain function value may be generated from a gain function (using SPPs) and used to adjust the error in gain, which is used to determine the glucose concentration from the point-of-interest glucose signal, as well as for error due to ISF glucose lag. In some embodiments, if each and every glucose reading in a CGM data continuum is determined accurately point-by-point by compensating and/or reducing error from signal deviation and from ISF lag, there will be little or no ISF lag relative to a reference glucose profile.

For example, a gain function value may be determined from a gain function that employs sensor progression parameters (SPPs), which are calculated from the present, point-of-interest glucose signal and previously-measured glucose signals (e.g., using ratios, differences, etc., as described below). That is, a gain function may be a function of SPPs (i.e., gain function=f(SPPs)). For example, the working electrode current signals and/or background current signals from a biosensor (e.g., a CGM sensor) may be periodically sampled and stored in a memory. For a subsequent, point-of-interest glucose signal (e.g., working electrode current signal), the stored current signals may be used with the point-of-interest glucose signal to calculate a gain function value from the gain function. The gain function value may then be used during a glucose concentration calculation for the point-of-interest glucose signal, to reduce error in the calculated glucose concentration for the point-of-interest glucose signal (e.g., by adjusting system gain using the gain function value).

As described further below gain functions may be determined, for example, using a statistical technique such as multivariate regression. In some embodiments, gain functions are pre-determined by a CGM device manufacturer and stored in a memory of a CGM device for use during glucose monitoring with the CGM device.

In one or more embodiments, a method may include generating a series of sensor progression parameters by taking the ratios of the glucose signal from a current data point to the glucose signals of prior data points. These ratios, and/or combinations of these ratios and/or other related terms, may be employed within a predetermined gain function that allows error compensation for error sources in CGM glucose signals, such as gain changes over time and ISF lag. This may increase CGM accuracy and/or assist with therapeutic actions taken in response to CGM glucose measurements. Biosensor systems in accordance with these and other embodiments are provided.

While described primarily with regarding to glucose concentration determinations during continuous glucose monitoring, it will be understood that embodiments described herein may be used with other continuous analyte monitoring systems (e.g., cholesterol, lactate, uric acid, alcohol, or other analyte monitoring systems).

As an example, one or more gain functions may be developed that include selected groups of sensor progression parameters such as ratios based on glucose signals taken at different times, combinations of such ratios, and other cross terms in a linear combination. Cross terms may include, for example, terms of SPPs (e.g., ratios, differences, etc.) in a relationship to other types of parameters, such as the initial glucose ($G_{RAW}$), normalized gains, background/interference signals, motion parameters, temperature values, a different ratio and/or the like. Non-linear combinations may also be employed. A sample gain function may take the form:

$$\text{Gain Function} = c_1 * R\_t1 + c_2 * R\_t2 + c_3 * R\_t3 + c_4 * R\_t4 + \ldots c_n * R\_tn \qquad (1)$$

where $c_1, c_2, c_3, c_4 \ldots c_n$ are weighted coefficients and $R\_t1$, $R\_t2$, $R\_t3$, $R\_t4 \ldots R\_tn$, are ratios of glucose data points taken at different times (e.g., a "point-of-interest" glucose data point divided by glucose data points measured and/or sensed prior to the point-of-interest glucose data point), combinations of ratios of glucose data points, or other cross terms. Thus, a gain function is a representation of the relative error in gain, and/or the relative error in glucose, and is derived from information gathered in the form of sensor progression parameters from a present (point-of-interest) glucose signal and previously-measured glucose signals (e.g., glucose signals measured a few minutes to up to 12 hours or more prior to the present glucose signal, in some embodiments). More specifically, in some embodiments, a gain function may be derived by multivariate regression or another statistical analysis technique from sensor progression parameters in the form of ratios, differences and/or relative differences of present glucose signals to past glucose signals, and their cross terms with one another and/or other parameters. In some embodiments, gain functions may be based on and/or include tens or even hundreds (or more) of sensor progression parameters such as ratios, differences, relative differences and/or cross terms. Examples gain functions and methods for determining such gain functions are described below.

In accordance with embodiments provided herein, the error in a raw or uncompensated glucose signal Signal$_{Raw}$ may be compensated for and/or otherwise corrected by using sensor progression parameters which reference the present data point to past data points in a gain function. For example, in some embodiments, a compensated glucose signal G$_{Comp}$ may be computed as:

$$G_{Comp}=\text{Signal}_{Raw}*\text{Gain}*(1/(1+\text{Gain Function})) \quad (2)$$

where Gain represents (system) gain determined from an in-situ calibration, for example, such as by dividing a calibration glucose value (G$_{BGM}$) from a blood glucose meter by a CGM sensor current (Signal$_{CGM}$), Gain=G$_{BGM}$/Signal$_{CGM}$.

In some embodiments, one or more gain functions may be determined and stored in a memory of a CGM device, such as a wearable or other portion of a CGM device, and used to compute compensated glucose values based on sensor progression parameters such as glucose signal ratios (and/or other relationships) and uncompensated glucose signals measured with an interstitial CGM sensor.

The conventional expression for BGM accuracy is that of percentage within a ±x % accuracy limit, such as ±20%, ±15%, or ±10%, which expresses the percentage difference of BGM glucose values relative to a reference glucose value (100%*[G$_{BGM}$−G$_{Ref}$]/G$_{Ref}$), and determines the percentage of data points falling within a certain accuracy limit in a sample population. The smaller the accuracy limit, the better the accuracy.

For CGM glucose determinations, the measurement accuracy may be defined by the Mean Absolute Relative Difference (MARD):

$$\text{MARD}=\Sigma[\text{Abs}([G_{CGM}-G_{REF}]/G_{REF})]/n) \quad (3)$$

wherein G$_{CGM}$ is the CGM measured glucose value, G$_{REF}$ is the reference glucose value, measured by BGM for example, and n is the number of data points. The expression of MARD combines the mean and standard deviation of a sample population against the reference glucose values to produce a composite MARD value, where the smaller the MARD value, the better the accuracy. While the BGM convention of accuracy has not been used for evaluating the error within a certain accuracy limit, one may approximate that the intrinsic accuracy expressed in terms of percentage within a ±x % accuracy limit, depending on the mean and standard deviation of the error in a data population, is about 2.5 times the MARD value. Thus, a 10% MARD value may have an approximate accuracy of data within ±25%, or an approximate 25% accuracy. Conversely, a BGM system having an accuracy of ±10% would be projected to have a MARD value of 4%. Embodiments described herein may allow reduced MARD values for CGM devices (e.g., about 7-10% or lower in some embodiments).

In accordance with embodiments provided herein, sensor progression parameters referencing a present (point-of-interest) data point to previously-measured data points may be expressed by ratios of the signal from the present data point to the signals of previously-measured data points. This may form a network of information embedded in the sensor progression parameters, which is fed into the calculation of the CGM glucose value of the present data point to improve accuracy. Ratios formed from the current or present data point and prior data points are sometimes referred to herein as "present-past ratios" for convenience. Present-past ratios may be calculated for working electrode current Iw, background current Ib, and Iw−Ib, or for optical signals such as fluorescence, absorbance and/or reflectance signals, and/or the like.

FIG. 1A illustrates referencing a present data point to past data points in a collection of glucose signals taken over a three-hour period, and use of the collected glucose signals to compute sensor progression parameters such as ratios in accordance with embodiments described herein. With reference to FIG. 1A, past glucose signal data points measured 3 hours, 2 hours, 1 hour, 9 minutes, 6 minutes and 3 minutes before the presently-measured glucose signal data point are shown (by the circles above R_3hr, R_2hr, R_1hr, R_9min, R_6min and R_3min, respectively). These past data points may be used to compute ratios for the present data point (referred to as R_3hr, R_2hr, R_1hr, R_9min, R_6min and R_3min in FIG. 1A). Other numbers of ratios may be calculated and/or increments of time may be used. Ratios for future data points may be similarly calculated as CGM sensing progresses during the CGM operation. Ratios using even "older" data points may be used, such as data points taken, 4, 8 or even 12 hours earlier, as indicated by R_4hr, R_8hr and R_12hr, respectively, in FIG. 1B. Longer or shorter ranges of past data points may be used.

Examples of present-past ratios are shown below, wherein Iw$_t$ represents a present data point at time t (the point-of-interest time) for the working electrode current, and Iw$_{t-xmin}$ represents a past data point at time t-xmin for the working electrode current measured x minutes before the present data point. For example, the present-past ratio, R_3min, for working electrode current based on the present working electrode current and the working electrode current 3 minutes earlier is:

$$R\_3\text{min}=Iw_t/Iw_{t-3min} \quad (4)$$

In this particular case, the data points are taken at a regular 3-minute interval. Longer term ratios may be based on times that are multiples of 3 minutes. For instance, the present-past ratios for working electrode current 6 minutes, 9 minutes, 1 hour, 3 hours and 12 hours earlier than a present, point-of-interest working electrode current are shown below in equations (5)-(9), respectively.

$$R\_6\text{min}=Iw_t/Iw_{t-6min} \quad (5)$$

$$R\_9\text{min}=Iw_t/Iw_{t-9min} \quad (6)$$

$$R\_1\text{hr}=Iw_t/Iw_{t-1hr} \quad (7)$$

$$R\_3\text{hr}=Iw_t/Iw_{t-3hr} \quad (8)$$

$$R\_12\text{hr}=Iw_t/Iw_{t-12hr} \quad (9)$$

Other measurement intervals may be used. For example, if the data acquisition rate is based on measurements taken every 5, 10, or 15 minutes, then the present-past ratios may be at multiples of 5, 10, or 15 minutes. Similar ratios may be determined for background current Ib, the current differential between working electrode and background currents, or the like, as shown, for example, by expressions (10)-(17) below:

$$R\_6\text{min}=Ib_t/Ib_{t-6min} \quad (10)$$

$$R\_9\text{min}=Ib_t/Ib_{t-9min} \quad (11)$$

$$R\_1\text{h}=Ib_t/Ib_{t-1hr} \quad (12)$$

$$R\_3\text{h}=Ib_t/Ib_{t-3hr} \quad (13)$$

$$R\_6\text{min}=(Iw_t-Ib_t)/(Iw_{t-6min}-Ib_{t-6min}) \quad (14)$$

$$R\_9\text{min}=(Iw_t-Ib_t)/(Iw_{t-9min}-Ib_{t-9min}) \quad (15)$$

$$R\_1\text{h}=(Iw_t-Ib_t)/(Iw_{t-1hr}-Ib_{t-1hr}) \quad (16)$$

$$R\_3\text{h}=(Iw_t-Ib_t)/(Iw_{t-3hr}-Ib_{t-3hr}) \quad (17)$$

Cross terms that include combinations of ratios and other parameters, and/or combinations of multiple ratios, also may be determined as described further below. Thus, for each measured data point, there is a set of parameters associated with the measured data point that may be obtained using prior data points. As stated, for sensor progression parameters, a present or "point-of-interest" glucose signal may be referenced to past glucose signals measured as far back as 6 hours, 8 hours, 10 hours or even 12 hours or longer before the point-of-interest glucose signal was measured. Sensor progression parameters may be calculated, in some embodiments, in terms of ratios, differences or other relationships between a present (point-of-interest) glucose signal and prior-measured glucose signals, where signals may be electrochemical currents, or optical signals such as fluorescence, absorbance or reflectance.

In some cases, a warm up period may be employed after a CGM sensor is inserted into a patient (e.g., a 3-hour warmup period or a shorter or longer warm up period). In such cases, there may be a period of a few hours where only data points collected during the warm up period may be obtained (e.g., 3 hours or however long the warm up time is). After the warm up period, as more data points are collected, ratios or other sensor progression parameters may be calculated based on increasingly older data points (e.g., 4 hours, 5 hours, 6 hours, etc.). In some embodiments, sensor progression parameters may be calculated using a present glucose signal and past glucose signals measured up to 12 hours previously. Other cut-off points may be used (e.g., longer or shorter than 12 hours).

FIGS. 1C, 1D and 1E illustrate tables 100a, 100b and 110c of example ratios for working electrode current Iw, background electrode current Ib, and Iw–Ib current differential, respectively, of a CGM sensor using prior data points measured up to 1 hour before the last data point (taken at Time=1 hour), in accordance with embodiments provided herein. The labeling of the ratios in Table 100a (e.g., w_3min, w_6min, etc.) specifies that the ratios are from working electrode (e.g., enzyme electrode) currents Iw. The labeling of the ratios in Table 100b specifies that the ratios are from the background currents Ib, and the labeling of the ratios in Table 100c specifies that the ratios are from Iw–Ib current values. For each row, ratios are computed by dividing the leftmost data point by the data points measured previously. For example, the most recent Iw, Ib or Iw–Ib signal (taken at Time=1 hour) is divided by previously measured current signals (in 3-minute intervals extending back to Time=0 hour). As can be seen in Tables 100a, 100b and 100c, a large number of ratios may be developed for each measured glucose signal based on previously measured glucose signals.

Different sensor progression parameters contain different information for a present signal, based on the particular previously-measured signals used. For example, FIG. 1F illustrates a graph 100d of example ratios versus elapsed time for working electrode current signals taken over a period of 50 hours, computed by dividing each working electrode current signal by the working electrode current signal measured 3-minutes, 30 minutes and 2 hours earlier (w_3min, w_30min and w_2hr, respectively). In this plot, the different ratios at any time t have different magnitudes, leading to the different temporal profiles of the sensor progression parameters. As shown in FIG. 1F, at each point in time, there are different ratios representing different information from prior data points that may be used to increase the accuracy of glucose determinations (as described below).

Figure 2:
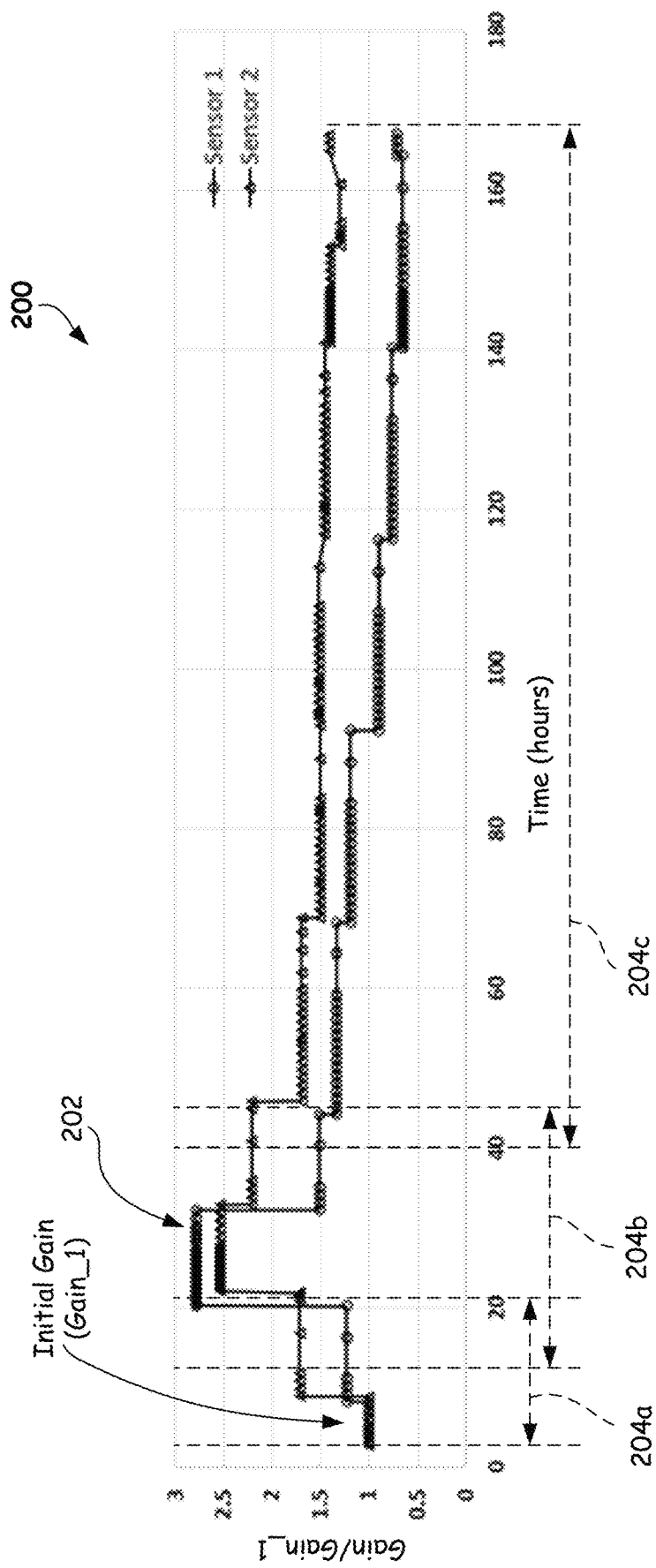
FIG. 2 illustrates a graph of example normalized Gain versus time for a series of in-situ calibrations for two CGM sensors (Sensor 1 and Sensor 2), in accordance with embodiments provided herein.

As mentioned earlier, there are two major sources of error during CGM measurements, the signal error and the ISF glucose lag. The first error source, the signal error, may be attributed to the sensitivity change over time or even sensitivity change within a calibration period. This can be seen in FIG. 2, which illustrates a graph 200 of example normalized Gain versus time for a series of in-situ CGM calibrations for two CGM sensors (Sensor 1 and Sensor 2), in accordance with embodiments provided herein. Specifically, each plateau or horizontal region, such as plateau 202 in FIG. 2, represents a normalized Gain calculated by dividing the BGM glucose value determined using a blood glucose meter by the glucose signal (e.g., Iw or Iw–Ib) of the CGM sensor (sensor 1 or sensor 2), and then dividing this Gain by the initial Gain (referred to as Gain_1). For example, per equation (18) below:

$$\text{Gain} = G_{Ref\text{-}cal}/\text{Signal}_{cal} \tag{18}$$

where $G_{Ref\text{-}cal}$ is a reference glucose value from a blood glucose meter and $\text{Signal}_{cal}$ is the raw glucose signal measured from a CGM sensor (e.g., working electrode current, working electrode current minus background electrode current or the like). Gain_1 is the initial Gain for the CGM sensor:

$$\text{Gain\_1} = G_{Ref\text{-}cal\_1}/\text{Signal}_{cal\_1} \tag{19}$$

so that Normalized Gain, Gain/Gain_1, becomes:

$$\text{Gain}/\text{Gain\_1} = (G_{Ref\text{-}cal}/\text{Signal}_{cal})/(G_{Ref\text{-}cal\_1}/\text{Signal}_{cal\_1}) \tag{20}$$

The Gain (also referred to as system gain) is defined analogous to electronic gain, having a physical dimension of [concentration/signal]. Thus, if the BGM concentration is in [mg/dL] and the sensor current signal is in [nanoAmps or nA], then the unit of the Gain is $[mg/dL][nA]^{-1}$.

Each stepwise gain in the Gain curve 200 of FIG. 2 represents a Gain used to convert the CGM sensor signal to a glucose concentration, which may be carried out by the expression:

$$G_{Raw} = \text{Gain} * \text{Signal} \tag{21}$$

where $G_{Raw}$ represents the initial (uncompensated) glucose value, Gain is the calibration-determined Gain ($G_{Ref\text{-}cal}/\text{Signal}_{cal}$) and Signal is the glucose signal from the CGM sensor (e.g., Iw or Iw–Ib).

By providing a series of in-situ calibrations, a set of Gains forms the Gain curve of FIG. 2, which reflects sensor sensitivity change and provides sectional calibrations to the CGM sensor over the course of the CGM sensor deployment (e.g., typically about 1-2 weeks or 7-14 days). However, additional change in sensitivity between in-situ calibrations becomes a source of error in the long-term monitoring process. The gain curve of FIG. 2 is specific to the sensor employed and relies on in-situ calibrations (e.g., taken periodically during the CGM process) using reference glucose values, such as BGM glucose values. That is, the gain curve of FIG. 2 is computed and/or adjusted based on data points measured during a CGM process.

Figure 3A:
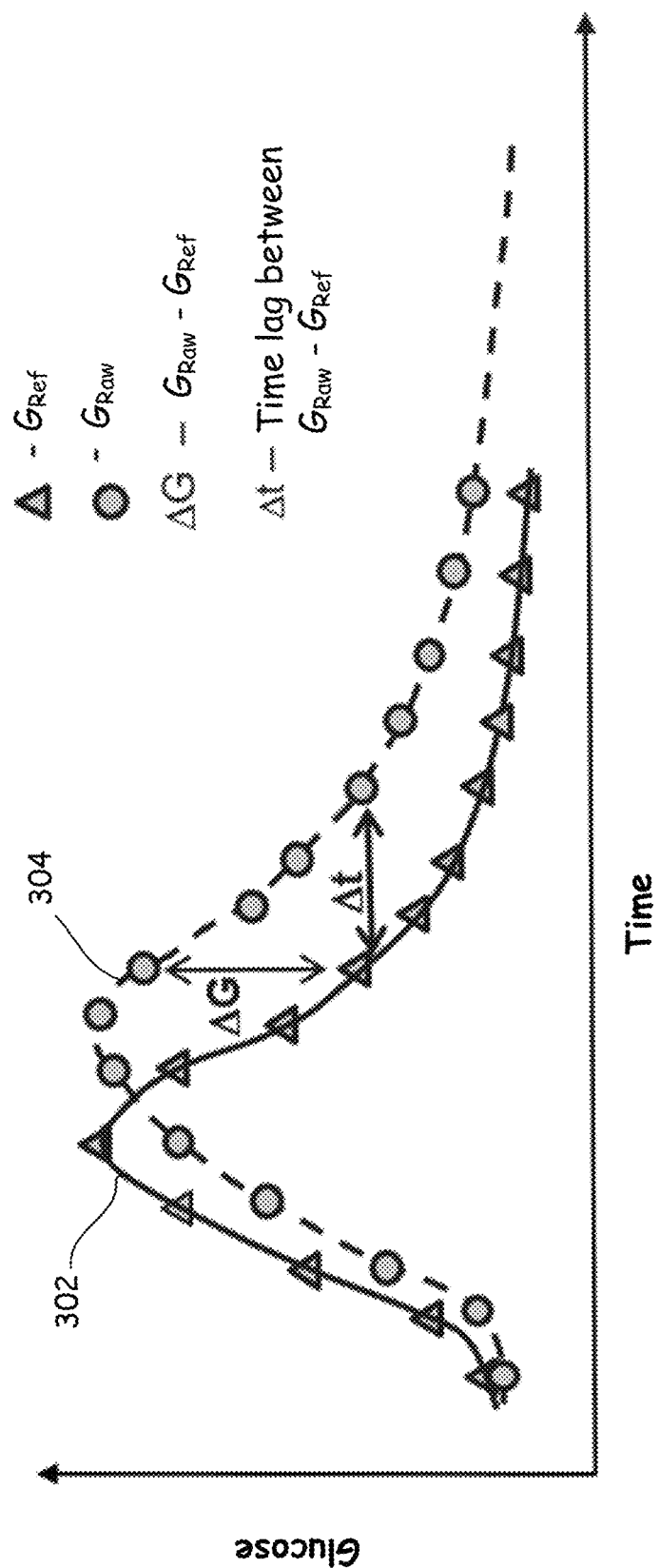
FIG. 3A illustrates graphs of glucose versus time as measured using BGM (capillary glucose) and CGM, in accordance with embodiments provided herein.

Another source of error is the apparent ISF (glucose) lag, which is depicted in a schematic drawing of FIG. 3A. In particular, FIG. 3A illustrates graphs of glucose versus time as measured using BGM (the reference glucose profile, Curve 302) and CGM (the CGM glucose profile, Curve 304). When considering the glucose profile from a reference (BGM) glucose measurement and the glucose profile from a CGM sensor, the glucose profiles of the two are separated or shifted such that there is a time lag wherein the ISF (CGM) glucose profile (Curve 304) is delayed by time lag Δt relative to the reference (BGM) glucose profile (Curve 302). The time lag Δt varies, depending on whether glucose was measured during a fasting or a glucose changing stage. As mentioned previously, a conventional method of reducing this time lag is by filtering, or lag-compensation. However, while these methods may work to some extent, the time lag may still exist due to the varying nature of the time lag.

As shown in FIG. 3A, and in accordance with embodiments described herein, if each individual error in glucose concentration ΔG on the CGM glucose profile is reduced/eliminated, then there is no obvious shift of the CGM glucose profile (Curve 304) from the reference (BGM) glucose profile (Curve 302). This point-by-point error compensation allows for improvement in the accuracy of CGM glucose measurements as described further below.

From the relationship $G_{Raw}$=Gain*Signal, it can be shown that the relative change in glucose ΔG/G is equal to the relative change in the sensor conversion Gain, ΔGain/Gain, holding Signal constant. That is:

$$\Delta G / G = \Delta \text{Gain}/\text{Gain} \qquad (22)$$
$$= (\text{Gain}_{act} - \text{Gain}_{cal})/\text{Gain}_{cal}$$
$$= \text{Gain}_{act}/\text{Gain}_{cal} - 1$$

where $\text{Gain}_{act}$ is the actual Gain accounting entirely for the error in the CGM system while $\text{Gain}_{cal}$ is the Gain from the in-situ calibration (e.g., a finger stick reading from a BGM). $\text{Gain}_{act}$ may be determined by $\text{Gain}_{act}=G_{BGM}/\text{Signal}_{act}$ from a paired data point (e.g., glucose signal and reference glucose value) within one calibration period in a study. In contrast, $\text{Gain}_{cal}$ may be determined after each in-situ calibration (a $\text{Gain}_{cal}$ is obtained as $\text{Gain}_{cal}=BGM_{cal}/\text{Signal}_{cal}$). $\text{Gain}_{act}$ and $\text{Gain}_{cal}$ may be identical if there is no error, or they may be different if any error is present. At the same time, the relative change in glucose ΔG/G is also equal to the relative change of the signal, holding the gain constant:

$$\Delta \text{Signal}/\text{Signal} = (\text{Signal}_{act} - \text{Signal}_{ideal})/\text{Signal}_{ideal} \qquad (23)$$
$$= \text{Signal}_{act}/\text{Signal}_{ideal} - 1$$

where $\text{Signal}_{act}$ is the real-world signal containing a portion of error which would lead to the error in actual glucose $G_{act}$ while $\text{Signal}_{ideal}$ is the ideal (error-free) signal giving the error-free glucose measurement using the calibration gain $\text{Gain}_{cal}$. In each of the above, relative changes in the glucose, the Gain and the signal, are referenced (via the denominator term) to the ideal, the calibrated, or true value. It can be seen from equation (21) that the relative change in Gain will be opposite to the relative change in Signal, holding glucose constant. This can also be seen from equations (22) and (23) wherein the perfect gain $\text{Gain}_{act}$ (accounting for all system error) in equation (22) resides in the numerator, while the ideal signal $\text{Signal}_{ideal}$ resides in the denominator of equation (23). This means that the relative signal error ΔSignal/Signal is equal but opposite in direction to the relative Gain change ΔGain/Gain. It is postulated that any change in signal, ΔSignal/Signal, may be attributable to the change in the sensor Gain, ΔGain/Gain, but in the opposite direction. As such, $\text{Gain}_{cal}$ may be adjusted to $\text{Gain}_{cal}/(1+\Delta\text{Gain}/\text{Gain})$ to account for the signal error. Thus, the final glucose value $G_{final}$ becomes:

$$G_{final}=\text{Signal}*\text{Gain}/(1+\Delta\text{Gain}/\text{Gain}) \qquad (24)$$

where the modifying factor 1/(1+ΔGain/Gain) expresses the relative change of the Gain defining the instant calibration status, but in the opposite direction to the relative signal change. $G_{final}$ may also be referred to herein as the compensated glucose value $G_{comp}$, and Signal may be referred to as the raw or uncompensated glucose signal $\text{Signal}_{Raw}$. Equation (24) may then be written as $G_{comp}=\text{Signal}_{Raw}*\text{Gain}*(1/(1+\text{Gain Function}))$, which is equation (2) above. For conversion functions having a nonlinear relationship or stepwise calculations of analyte concentrations, the compensation relationship may be expressed as:

$$G_{comp}=G_{raw}/(1+\text{Gain Function}), \qquad (25)$$

where $G_{raw}$ is the initial glucose determination from these other conversion functions.

Figure 3B:
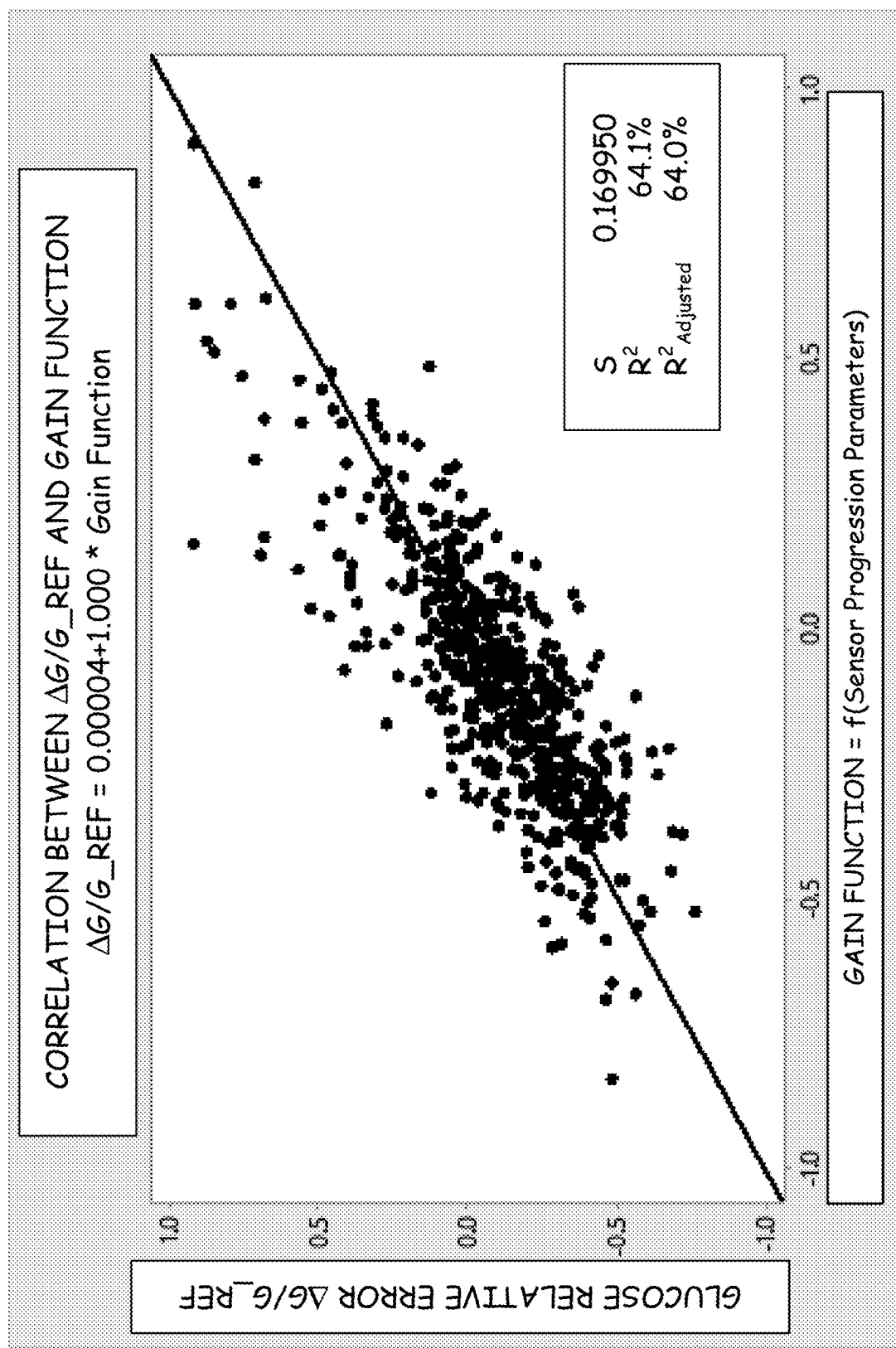
FIG. 3B illustrates a graph of ΔG/G (or ΔGain/Gain) versus Gain Function derived by multivariate regression from a clinical study data set, in accordance with embodiments provided herein.

Given the above relationship for $G_{Final}=\text{Signal}_{Raw}*\text{Gain}/(1+\Delta\text{Gain}/\text{Gain})$, the goal is to find the sensor progression parameters, such as ratios or other parameters, that fulfill and/or define the gain function ΔGain/Gain. From the previous discussion of present-past ratios as the information gathered from prior data points, in some embodiments, the gain function may be derived from these ratios and their cross terms. There may not be any explicit or apparent correlation of any single ratio and the gain function ΔGain/Gain, or the relative glucose change ΔG/G. However, multiple numbers of ratio terms and their selective cross terms collectively may provide the requisite correlation between the relative gain change and the gain function ΔGain/Gain. For example, in some embodiments, multivariate regression may be employed with ΔGain/Gain or ΔG/G as the regression target and a large number of present-past ratios terms and cross terms as the input parameters providing information gathered from prior data points. In some embodiments, up to 2000 or more combined terms of present-past ratio terms and/or cross terms may be employed as input parameters. Fewer or more ratio terms and/or cross terms may be employed, as may other relationships between present (point-of-interest) data points and previous data points (e.g., differences or other relationships). FIG. 3B shows a correlation between the relative glucose error ΔG/G and the gain function defined by a group of ratios and their cross terms. The gain function is a function of sensor progression parameters (SPPs); that is, gain function=f(SPPs). The $R^2$=64% indicates a strong correlation. A larger $R^2$ value indicates a stronger correlation, and the more accurately the gain function will approach the relative gain change (and the better the compensation results will be based on the gain function).

As an example, 167 hours of CGM data was collected for several dozen users, using numerous CGM sensors. The entire course of 167 hours of CGM data was divided into three segments: (1) 3 to 21 hours, (2) 12-45 hours, (3) 40-167 hours. These segments are identified in the gain curves of FIG. 2 by reference numerals 204a, 204b and 204c, respectively. Fewer or more segments may be used. Referring to FIG. 2, the largest change in gain occurs within the second segment 204b. For the first segment 204a ratios using previous data points taken up to 3 hours prior to a point-of-interest signal (due to the warm up time of 3-hour) may be employed. For example, in some embodiments, data collected during the warm up period may be used to calculate present-past ratios starting at 3 hours. For the second segment 204b, ratios using previous data points taken up to 12 hours prior to a point-of-interest signal may be employed, with focus on the relatively large change in the Gain. For the third segment 204c, previous data points taken up to 12 hours prior to a point-of-interest signal may be employed. As stated, older prior data points may be used.

Multivariate regression may be performed using any suitable data analysis and/or statistics software package to obtain gain functions for each segment 204a, 204b and 204c. For example, Minitab software available from Minitab, LLC of State College, Pa. or another similar software package may be employed.

Using multivariate regression on individual data points and their ratio parameters, the following example gain functions may be determined. Other ratios, data point relationships, cross terms and/or gain functions may be employed.

FIGS. 4A, 4B and 4C illustrate example gain functions for segments 204a, 204b and 204c of FIG. 2 (referred to as Gain Function 1, Gain Function 2 and Gain Function 3 in FIGS. 4A-C) in accordance with embodiments described herein. FIGS. 4D, 4E and 4F are listings of definitions of sensor progression parameters (e.g., ratios) and cross terms for Gain Function 1, Gain Function 2 and Gain Function 3, respectively, in accordance with embodiments described herein. This information is also provided in the appendix section below. Other and/or other numbers of gain functions, sensor progression parameters, cross terms, coefficient values and/or constants may be employed. These gain functions and gain function terms are merely representative; other types and/or numbers of gain functions may be used.

In operation, gain functions may be stored in a memory of a CGM device and employed to generate the gain function value used to calculate a compensated glucose value based on a presently-measured glucose signal (e.g., working electrode current or an optical signal) from a CGM sensor and past glucose signals taken up to twelve hours or more before the presently-measured glucose signal. Use of such gain functions may significantly reduce the error in CGM glucose values caused by gain changes and ISF lag. For example, some uncompensated glucose values from CGM sensors have been observed to have MARD values of between 18%-25%, while compensated glucose values determined using gain functions have been observed to have MARD values of 7%-10% in accordance with embodiments described herein.

Figure 5A:
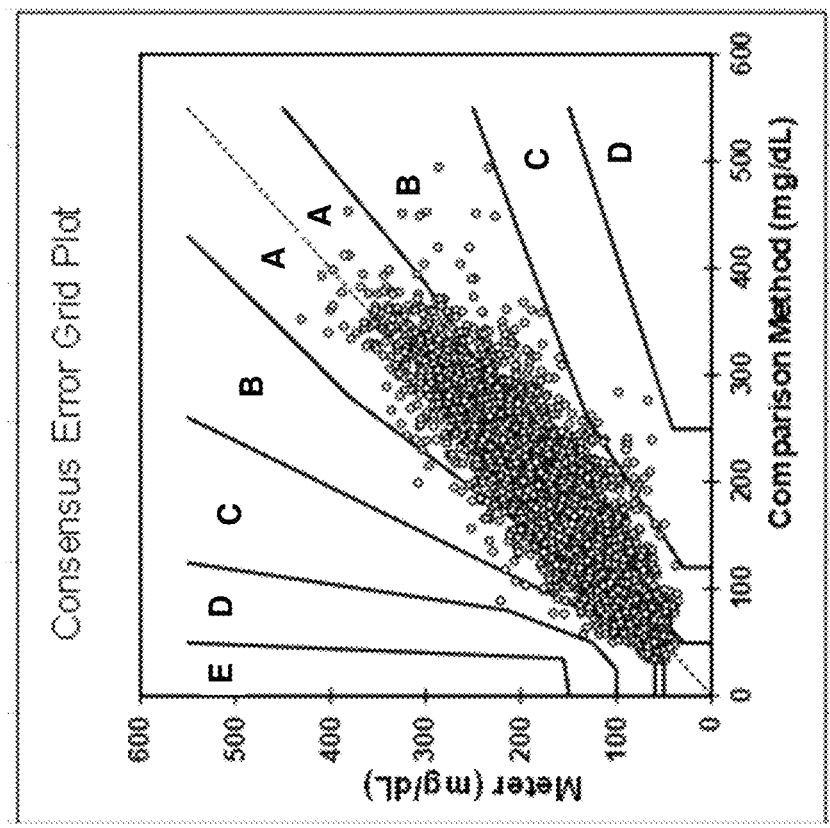
FIGS. 5A and 5B illustrate example consensus error grid plots for raw glucose values and compensated glucose values, respectively, of a CGM sensor in accordance with embodiments provided herein.
Figure 5B:
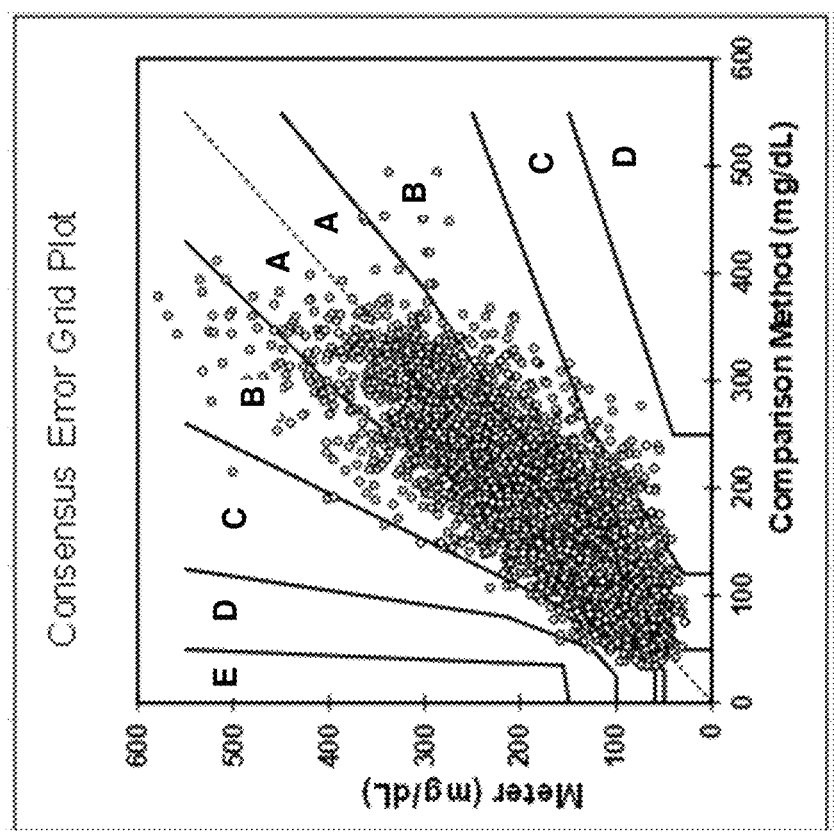

FIGS. 5A and 5B illustrate example consensus error grid plots 500a and 500b for raw glucose values and compensated glucose values, respectively, of a CGM sensor in accordance with embodiments provided herein. The clinical significance of Regions A, B, C, D, E is described below in Table 1 based on Joan L. Parkes et al., "A New Consensus Error Grid to Evaluate the Clinical Significance of Inaccuracies in the Measurement of Blood Glucose," Diabetes Care, Volume 23(8), pp. 1143-1148 (2000).

TABLE 1

| Region | Clinical Significance |
| --- | --- |
| A | Clinically accurate, no effect on clinical action. |
| B | Altered clinical action or little or no effect on clinical outcome. |
| C | Altered clinical action and likely to affect clinical outcome. |
| D | Altered clinical action and may have significant medical risk. |
| E | Altered clinical action and may have dangerous consequences. |

Figure 6A:
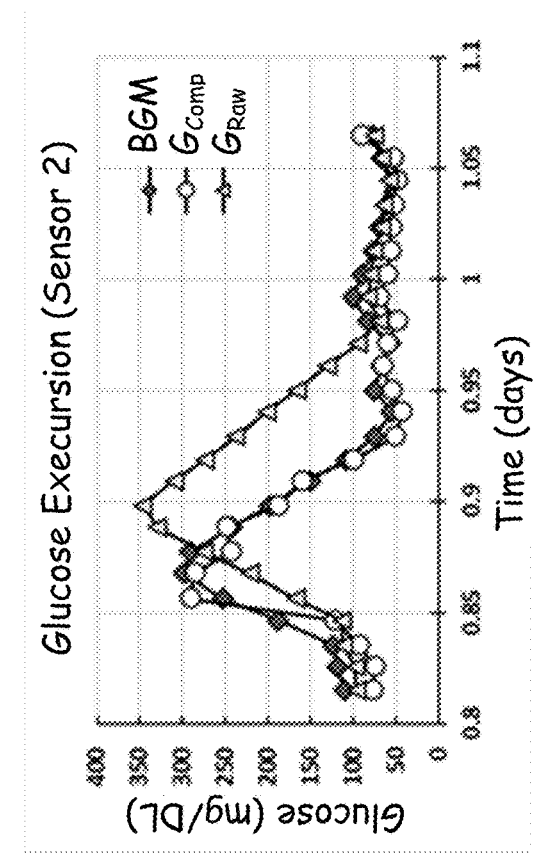
FIGS. 6A and 6B illustrate BGM glucose value, compensated CGM glucose value ($G_{Comp}$) and uncompensated CGM glucose value ($G_{Raw}$) vs. time for a first CGM sensor (Sensor 1 in FIG. 6A) and a second CGM sensor (Sensor 2 in FIG. 6B), in accordance with embodiments provided herein.
Figure 6B:
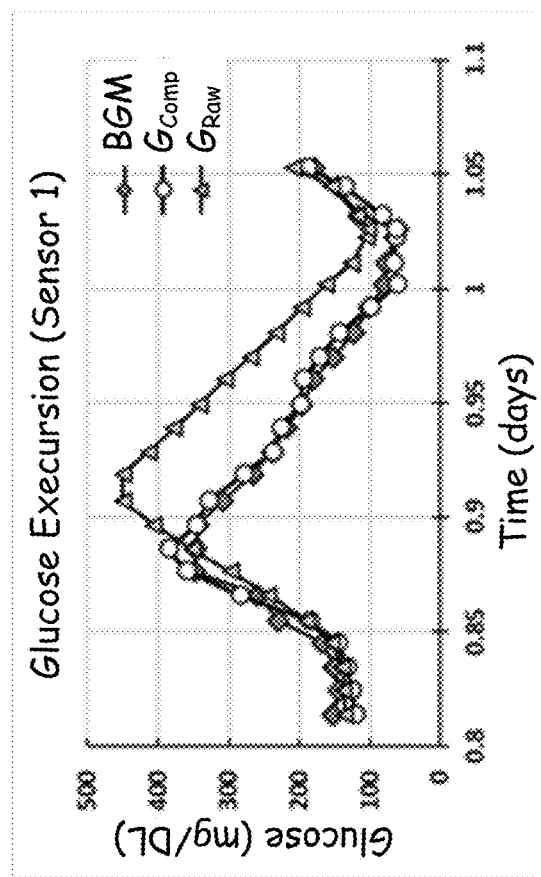

As shown in FIGS. 5A and 5B, the combined data in Regions A and B for glucose values with error compensation is greater than 99% (FIG. 5B) compared to less than 98% for uncompensated glucose values (FIG. 5A). Further, significantly more glucose values fall in Region A. This performance improvement may also be seen in the effective reduction in ISF lag for compensated CGM glucose values. For example, FIGS. 6A and 6B illustrate BGM glucose value, compensated CGM glucose value ($G_{Comp}$) and uncompensated CGM glucose value ($G_{Raw}$) vs. time for a first CGM sensor (Sensor 1 in FIG. 6A) and a second CGM sensor (Sensor 2 in FIG. 6B), in accordance with embodiments provided herein. By using gain functions, the compensated glucose values ($G_{Comp}$) for both CGM sensors appear essentially free of ISF lag in comparison to the raw glucose values ($G_{Raw}$).

Figure 7A:
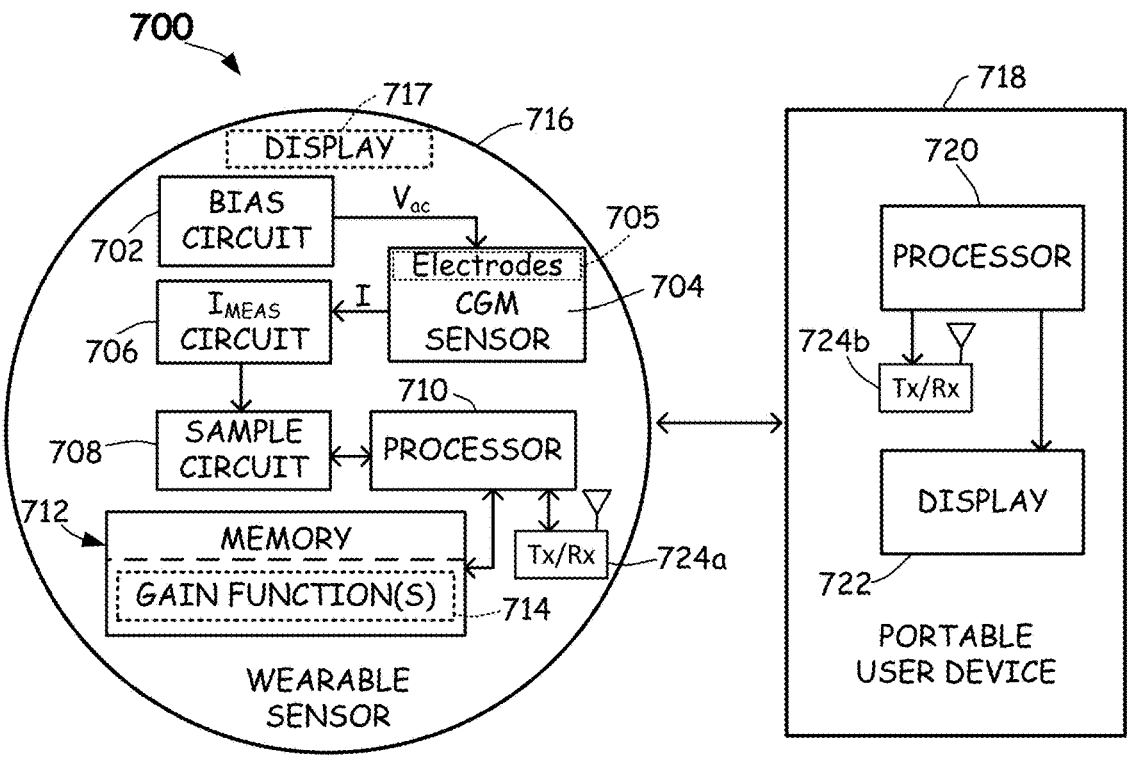
FIG. 7A illustrates a high-level block diagram of an example CGM device in accordance with embodiments provided herein.

FIG. 7A illustrates a high-level block diagram of an example CGM device 700 in accordance with embodiments provided herein. Although not shown in FIG. 7A, it is to be understood that the various electronic components and/or circuits are configured to couple to a power supply, such as but not limited to, a battery. CGM device 700 includes a bias circuit 702 that may be configured to couple to a CGM sensor 704. Bias circuit 702 may be configured to apply a bias voltage, such as a continuous DC bias, to an analyte-containing fluid through CGM sensor 704. In this example embodiment, the analyte-containing fluid may be human interstitial fluid, and the bias voltage may be applied to one or more electrodes 705 of CGM sensor 704 (e.g., a working electrode, a background electrode, etc.).

In some embodiments, the CGM sensor 704 may include two electrodes and the bias voltage may be applied across the pair of electrodes. In such cases, current may be measured through the CGM sensor 704. In other embodiments, the CGM sensor 704 may include three electrodes such as a working electrode, a counter electrode and a reference electrode. In such cases, the bias voltage may be applied between the working electrode and the reference electrode, and current may be measured through the working electrode, for example. The CGM sensor 704 includes chemicals which react with a glucose-containing solution in a reduction-oxidation reaction, which affects the concentration of charge carriers and the time-dependent impedance of the CGM sensor 704. Example chemicals include glucose oxidase, glucose dehydrogenase, or the like. In some embodiments, a mediator such as ferricyanide or ferrocene may be employed.

The bias voltage generated and/or applied by bias circuit 702 may range from about 0.1 to 1 volts versus the reference electrode, for example. Other bias voltages may be used.

A current through CGM sensor 704 in an analyte-containing fluid responsive to the bias voltage may be conveyed from CGM sensor 704 to a current measurement ($I_{meas}$) circuit 706 (also referred to as current sensing circuitry). Current measurement circuit 706 may be configured to sense and/or record a current measurement signal that has a magnitude indicative of the magnitude of the current conveyed from CGM sensor 704 (e.g., using a suitable current-to-voltage converter (CVC), for example). In some embodiments, current measurement circuit 706 may include a resistor having a known nominal value and a known nominal precision (e.g., 0.1% to 5%, or even smaller than 0.1%, in some embodiments), through which the current conveyed from CGM sensor 704 is passed. A voltage developed across the resistor of current measurement circuit 706 represents the magnitude of the current, and may be referred to as the current measurement signal (or raw glucose signal $Signal_{Raw}$).

In some embodiments, a sample circuit 708 may be coupled to current measurement circuit 706, and may be configured to sample the current measurement signal, and may produce digitized time-domain sample data that is representative of the current measurement signal (e.g., digitized glucose signals). For example, sample circuit 708 may be any suitable A/D converter circuit configured to receive the current measurement signal, which is an analog signal, and convert it to a digital signal having a desired number of bits as an output. The number of bits output by sample circuit 708 may be sixteen in some embodiments, but more or fewer bits may be used in other embodiments. In some embodiments, sample circuit 708 may sample the current measurement signal at a sampling rate in the range of about 10 samples per second to 1000 samples per second. Faster or slower sampling rates may be used. For example, sampling rates such as about 10 kHz to 100 kHz may be used and down-sampled to further reduce signal-to-noise ratio. Any suitable sampling circuitry may be employed.

Still referring to FIG. 7A, a processor 710 may be coupled to sample circuit 708, and may be further coupled to a memory 712. In some embodiments, processor 710 and sample circuit 708 are configured to directly communicate with each other via a wired pathway (e.g., via a serial or parallel connection). In other embodiments, the coupling of processor 710 and sample circuit 708 may be by way of memory 712. In this arrangement, sample circuit 708 writes digital data to memory 712, and processor 710 reads the digital data from memory 712.

Memory 712 may have stored therein one or more gain functions 714 for use in determining compensated glucose values based on raw glucose signals (from current measurement circuit 706 and/or sample circuit 708). For example, in some embodiments, three or more gain functions may be stored in memory 712, each for use with different segments (time periods) of CGM collected data, as previously described. Memory 712 also may have stored therein a plurality of instructions. In various embodiments, processor 710 may be a computational resource such as but not limited to a microprocessor, a microcontroller, an embedded microcontroller, a digital signal processor (DSP), a field programmable gate array (FPGA) configured to perform as a microcontroller, or the like.

In some embodiments, the plurality of instructions stored in memory 712 may include instructions that, when executed by the processor 710, cause the processor 710 to (a) cause the CGM device 700 (via bias circuit 702, CGM sensor 704, current measurement circuit 706 and/or sample circuit 708) to measure glucose signals (e.g., current signals) from interstitial fluid; (b) store glucose signals in memory 712; (c) compute sensor progression parameters such as ratios (and/or other relationships) of point-of-interest glucose signals to earlier measured glucose signals; (d) employ the computed sensor progression parameters and stored gain functions to compute compensated glucose values (e.g., concentrations); and (e) communicate the compensated glucose values to a user.

Memory 712 may be any suitable type of memory, such as but not limited to, one or more of a volatile memory and/or a non-volatile memory. Volatile memory may include, but is not limited to a static random access memory (SRAM), or a dynamic random access memory (DRAM). Non-volatile memory may include, but is not limited to, an electrically programmable read-only memory (EPROM), an electrically erasable programmable read-only memory (EEPROM), a flash memory (e.g., a type of EEPROM in either of the NOR or NAND configurations, and/or in either the stacked or planar arrangements, and/or in either the single-level cell (SLC), multi-level cell (MLC), or combination SLC/MLC arrangements), a resistive memory, a filamentary memory, a metal oxide memory, a phase change memory (such as a chalcogenide memory), or a magnetic memory. Memory 112 may be packaged as a single chip or as multiple chips, for example. In some embodiments, memory 112 may be embedded, with one or more other circuits, in an integrated circuit, such as, for example, an application specific integrated circuit (ASIC).

As noted above, memory 712 may have a plurality of instructions stored therein that, when executed by processor 710, cause processor 710 to perform various actions specified by one or more of the stored plurality of instructions. Memory 712 may further have portions reserved for one or more "scratchpad" storage regions that may be used for read or write operations by processor 710 responsive to execution of one or more instructions of the plurality of instructions.

In the embodiment of FIG. 7A, bias circuit 702, CGM sensor 704, current measurement circuit 706, sample circuit 708, processor 710, and memory 712 including gain functions 714, may be disposed within a wearable sensor portion 716 of CGM device 700. In some embodiments, wearable sensor portion 716 may include a display 717 for displaying information such as glucose concentration information (e.g., without use of external equipment). Display 717 may be any suitable type of human-perceivable display, such as but not limited to, a liquid crystal display (LCD), a light-emitting diode (LED) display, or an organic light emitting diode (OLED) display.

Still referring to FIG. 7A, CGM device 700 may further include a portable user device portion 718. A processor 720 and a display 722 may be disposed within portable user device portion 718. Display 722 may be coupled to processor 720. Processor 720 may control the text or images shown by display 722. Wearable sensor portion 716, and portable user device portion 718, may be communicatively coupled. In some embodiments the communicative coupling of wearable sensor portion 716, and portable user device portion 718, may be by way of wireless communication via transmitter circuitry and/or receiver circuitry, such as transmit/receive circuit TxRx 724a in wearable sensor portion 716 and transmit/receive circuit TxRx 724b in portable user device portion 718, for example. Such wireless communication may be by any suitable means including but not limited to standards-based communications protocols such as the Bluetooth® communications protocol. In various embodiments, wireless communication between wearable sensor portion 716, and portable user device portion 718, may alternatively be by way of near-field communication (NFC), radio frequency (RF) communication, infra-red (IR) communication, or optical communication. In some embodiments, wearable sensor portion 716 and portable user device portion 718 may be connected by one or more wires.

Display 722 may be any suitable type of human-perceivable display, such as but not limited to, a liquid crystal display (LCD), a light-emitting diode (LED) display, or an organic light emitting diode (OLED) display.

Figure 7B:
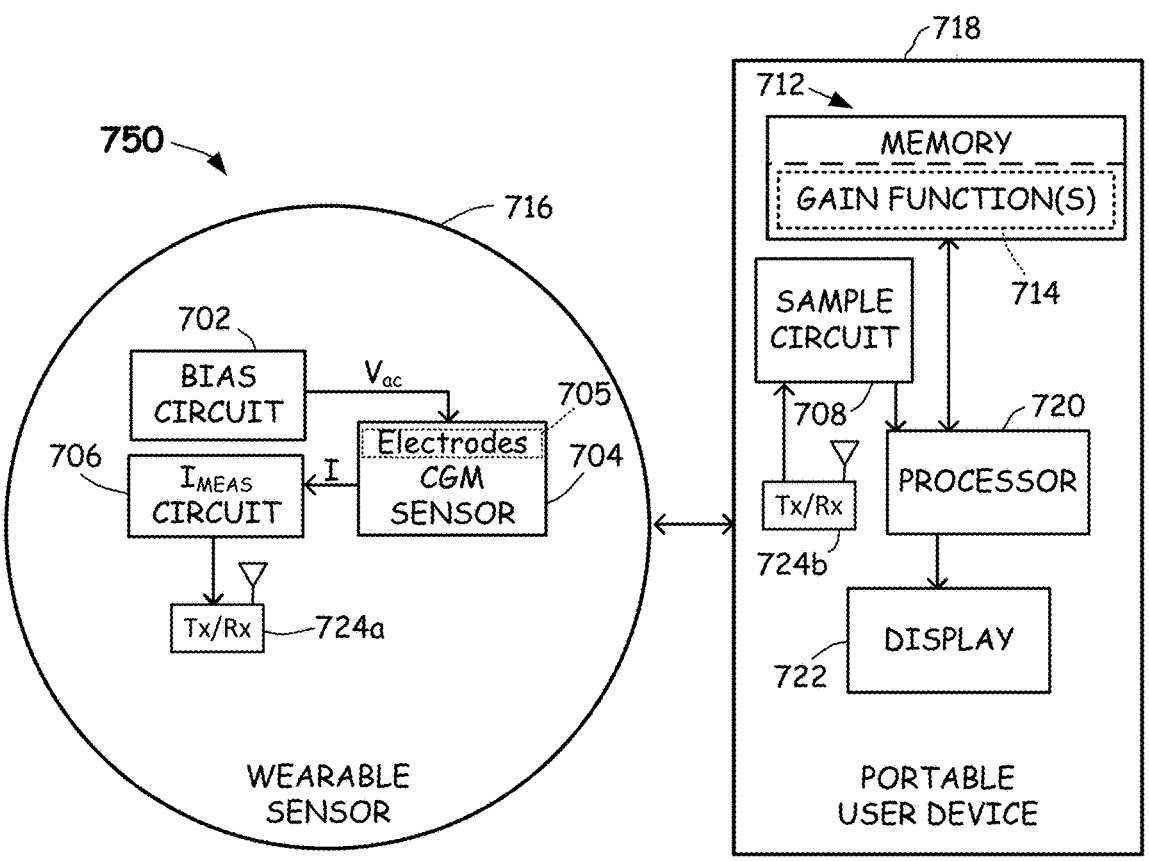
FIG. 7B illustrates a high-level block diagram of another example CGM device in accordance with embodiments provided herein.

Referring now to FIG. 7B, an example CGM device 750 is shown that is similar to the embodiment illustrated in FIG. 7A, but having a different partitioning of components. In CGM device 750, the wearable sensor portion 716 includes the bias circuit 702 coupled to the CGM sensor 704, and the current measurement circuit 706 coupled to the CGM sensor 704. The portable user device portion 718 of CGM device 750 includes the sample circuit 708 coupled to processor 720, and the display 722 coupled to processor 720. Processor 720 is further coupled to memory 712 that has the gain function(s) 714 stored therein. In some embodiments, processor 720 in CGM device 750 may also perform the previously-described functions performed by processor 710 of CGM device 700 of FIG. 7A, for example. Wearable sensor portion 716 of CGM device 750 may be smaller and lighter, and therefore less invasive, than CGM device 700 of FIG. 7A because sample circuit 708, processor 710, memory 712, etc., are not included therein. Other component configurations may be employed. For example, as a variation to the CGM device 750 of FIG. 7B, sample circuit 708 may remain on wearable sensor portion 716 (such that portable user device 718 receive digitize glucose signals from wearable sensor portion 716).

Figure 8:
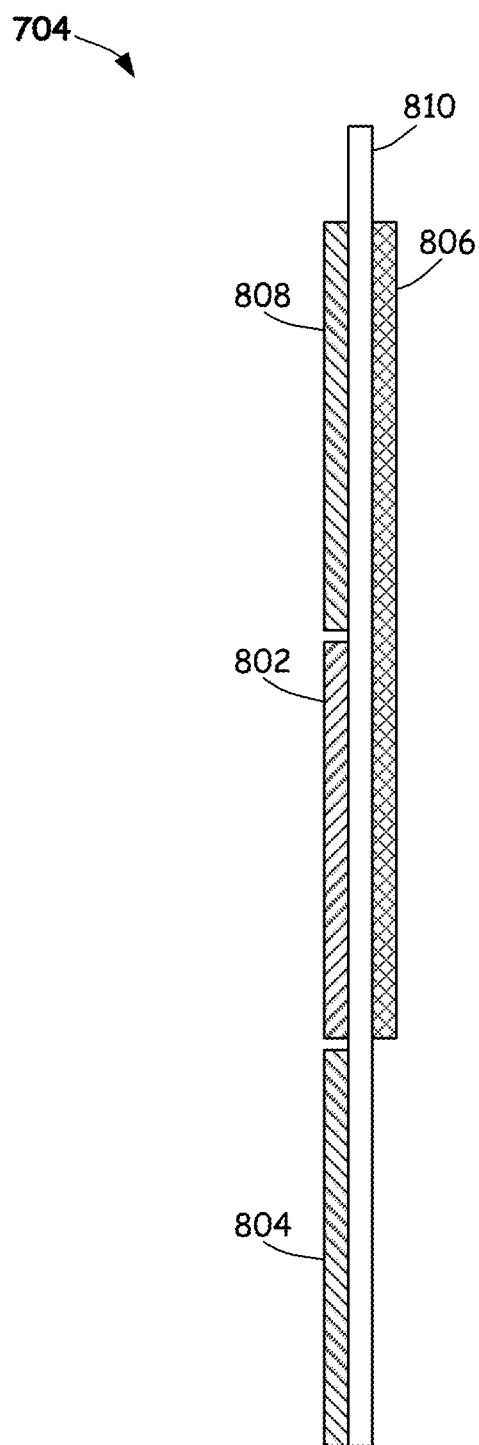
FIG. 8 is a side schematic view of an example glucose sensor in accordance with embodiments provided herein.

FIG. 8 is a side schematic view of an example glucose sensor 704 in accordance with embodiments provided herein. In some embodiments, glucose sensor 704 may include a working electrode 802, a reference electrode 804, a counter electrode 806 and a background electrode 808. The working electrode 802 may include a conductive layer coated with a chemical which reacts with a glucose-containing solution in a reduction-oxidation reaction (which affects the concentration of charge carriers and the time-dependent impedance of the CGM sensor 704). In some embodiments, the working electrode 802 may be formed from platinum or surface roughened platinum. Other working electrode materials may be used. Example chemical catalysts (e.g., enzymes) for the working electrode 802 include glucose oxidase, glucose dehydrogenase, or the like. The enzyme component may be immobilized onto the electrode surface by a cross-linking agent such as glutaraldehyde, for example. An outer membrane layer may be applied onto the enzyme layer to protect the overall inner components including the electrode and the enzyme layer. In some embodiments, a mediator such as ferricyanide or ferrocene may be employed. Other chemical catalysts and/or mediators may be employed.

In some embodiments, reference electrode 804 may be formed from Ag/AgCl. The counter electrode 806 and/or the background electrode 808 may be formed a suitable conductor such as platinum, gold, palladium, or the like. Other materials may be used for the reference, counter and/or background electrodes. In some embodiments, the background electrode 808 may be identical to the working electrode 802, but without the chemical catalyst and mediator. Counter electrode 806 may be isolated from the other electrodes by an isolation layer 810 (e.g., polyimide or another suitable material).

Figure 9:
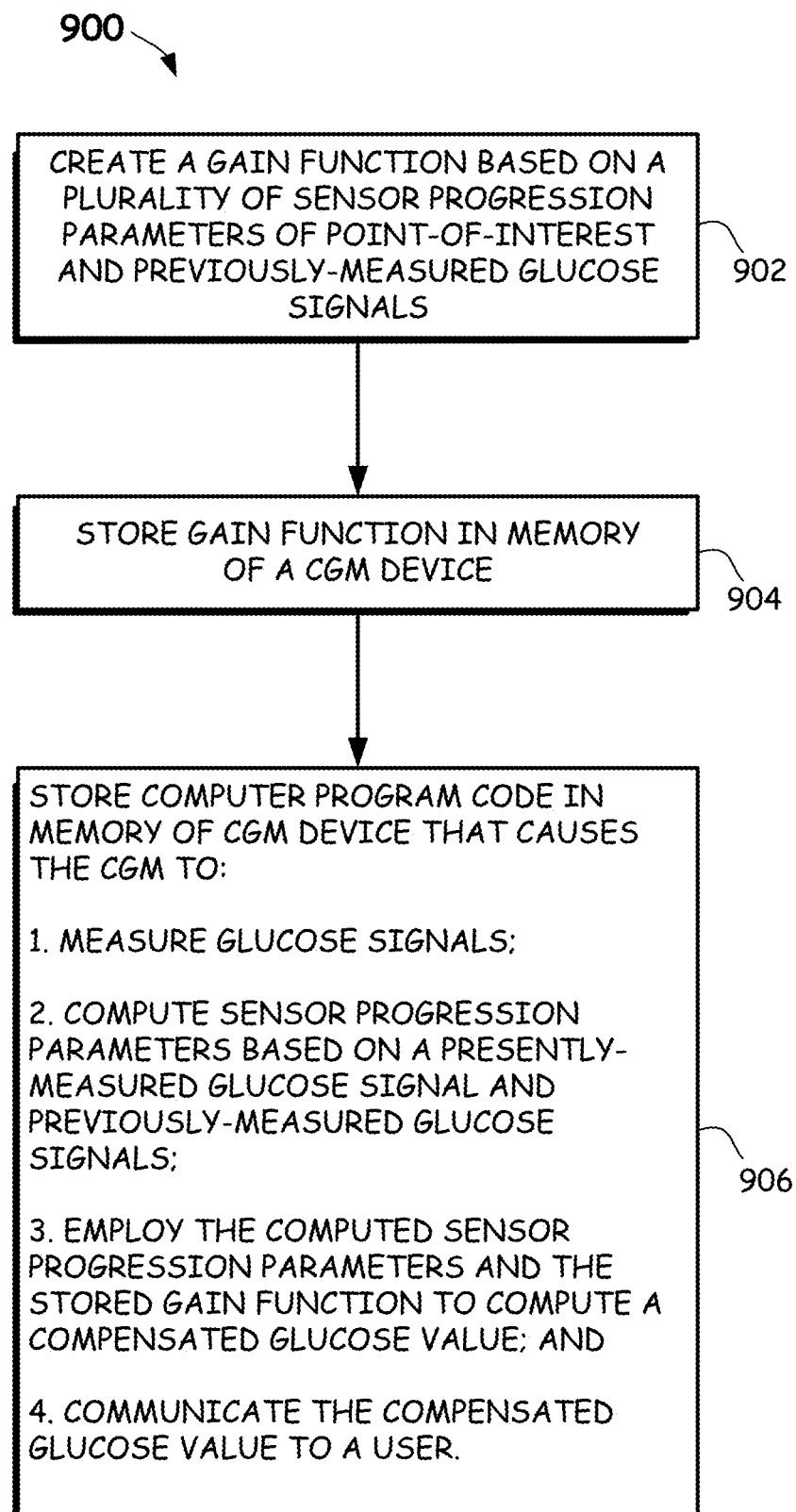
FIG. 9 is a flowchart of an example method of making a CGM device, in accordance with embodiments provided herein.

FIG. 9 is a flowchart of an example method 900 of making a CGM device in accordance with embodiments provided herein. With reference to FIG. 9, in Block 902, a gain function is created based on a plurality of sensor progression parameters, such as a plurality of ratios of glucose signals (measured by a CGM sensor). Glucose signals may be electrochemical currents, optical signals, or the like. Each sensor progression parameter (SPP) is based on a point-of-interest glucose signal and a glucose signal measured prior to the point-of-interest glucose signal. For example, a SPP ratio includes a ratio of a point-of-interest glucose signal and a glucose signal measured prior to the point-of-interest glucose signal. In some embodiments, glucose signals measured up to 12 hours before the point-of-interest glucose signal may be employed. Shorter or longer time periods may be used. In at least some embodiments, multivariate regression or a similar statistical technique may be employed with hundreds, or even thousands, of sensor progression parameters such as ratios, differences, etc., and/or other cross terms to compute the relevant SPPs (e.g., ratios, differences, etc.), cross terms and coefficients to employ in a gain function. Multiple gain functions (e.g., 2, 3, 4, 5, etc.) may be determined for use during different time periods of CGM monitoring. For example, one or more gain functions may be stored in memory 712 of wearable sensor portion 716 (FIG. 7A) or portable user device 718 (FIG. 7B).

In Block 904, the gain function is stored in a memory of a CGM device (e.g., in the form of the parameter names and their coefficients). For example, one or more gain functions may be stored in memory 712 of wearable sensor portion 716 (FIG. 7A) or portable user device 718 (FIG. 7B).

In Block 906, computer program code is stored in the memory of the CGM device which, when executed by a processor, causes the CGM device to (a) measure a plurality of glucose signals using the sensor of the CGM device; (b) store the glucose signals in the memory of the CGM device; (c) for a presently-measured glucose signal, compute a plurality of sensor progression parameters such as ratios, differences, etc., based on the presently-measured glucose signal and a plurality of previously-measured glucose signals stored in the memory; (d) employ the plurality of sensor progression parameters and the stored gain function to compute a compensated glucose value (e.g., concentration); and (e) communicate the compensated glucose value to a user of the CGM device. For example, computer program code may be stored in memory 712 of wearable sensor portion 716 (FIG. 7A) or portable user device 718 (FIG. 7B). The CGM sensor 704 may be used to measure glucose signals, which may be stored in memory 712. These stored glucose signals may be employed to compute a plurality of ratios for a presently-measured glucose signal. The computed ratios may then be employed with the stored gain function to compute a compensated glucose value (e.g., using processor 710, processor 720 and/or equation (2) above). Once computed, the compensated glucose value may be communicated to a user (e.g., via display 717 of wearable sensor 716 and/or display 722 of portable user device 718).

Figure 10:
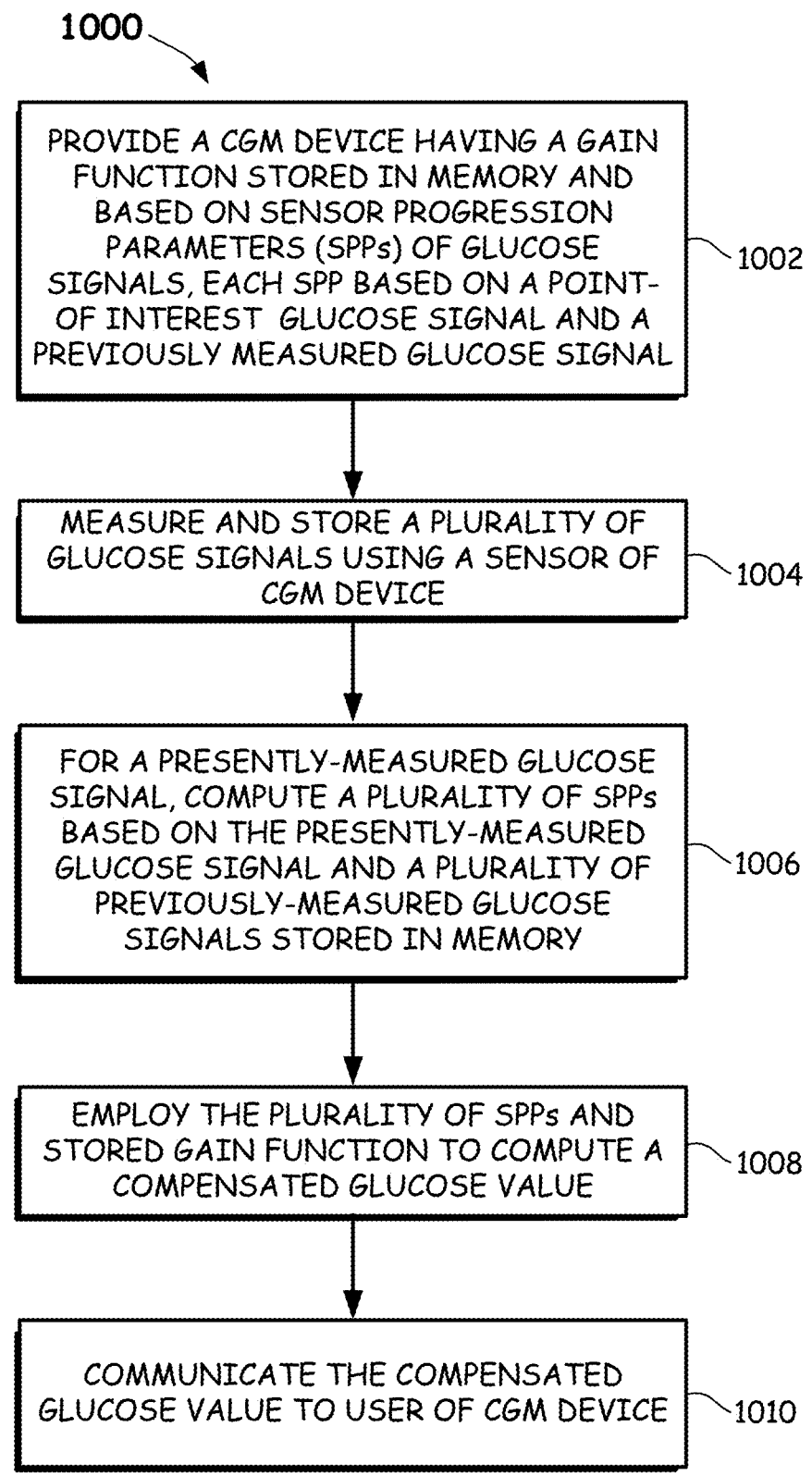
FIG. 10 is a flowchart of an example method of determining glucose concentration during continuous glucose monitoring measurements, in accordance with embodiments provided herein.

FIG. 10 is a flowchart of an example method 1000 of determining glucose concentration during continuous glucose monitoring (CGM) measurements, in accordance with embodiments provided herein. With reference to FIG. 10, in Block 1002, a CGM device is provided that includes a sensor, a memory and a processor. The CGM device includes one or more gain functions stored in the memory. Each gain function is based on a plurality of sensor progression parameters of glucose signals, such as ratios that each includes a ratio of a point-of-interest glucose signal and a glucose signal measured prior to the point-of-interest glucose signal. In some embodiments, glucose signals measured up to 12 hours before the point-of-interest glucose signal may be employed. Shorter or longer time periods may be used. For example, one or more gain functions may be stored in memory 712 of wearable sensor portion 716 (FIG. 7A) or portable user device 718 (FIG. 7B). Glucose signals may be electrochemical currents, optical signals, or the like. In any of the embodiments described herein, additional calibration information, such as in-situ and/or factory calibration data, may be stored in a CGM or other analyte monitoring device (e.g., in a memory of the device such as memory 712) for use during glucose and/or other analyte determinations.

In Block 1004, a plurality of glucose signals is measured and stored in the memory of the CGM device. For example, wearable sensor portion 716 may be applied to a user of CGM device 700 using a suitable inserter. During the insertion process, CGM sensor 704 is inserted through the skin of the user and contacts interstitial fluid. Bias circuit 702 may apply a bias voltage (e.g., a continuous DC bias) to CGM sensor 704, and current measurement circuit 706 may then sense the current signal generated by the applied bias voltage (e.g., working electrode current, and in some embodiments, background electrode current). Sample circuit 708 may digitize the sensed current signal(s), and processor 710 (or processor 720 in the embodiment of FIG. 7B) may store the current signal(s) in memory 712.

In Block 1006, a plurality of sensor progression parameters, such as a plurality of ratios, is calculated based on a presently-measured glucose signal and a plurality of previously-measured glucose signals stored in the memory of the CGM. For example, each sensor progression parameter employed by the gain function stored in the memory of the CGM device may be computed for the presently-measured glucose signal (e.g., using processor 710 or 720 and memory 712 of FIG. 7A or 7B).

In Block 1008, the calculated sensor progression parameters and stored gain function are used to compute a compensated glucose value based on the presently-measured glucose signal. As discussed, the gain function used may depend on the time period in which the presently-measured glucose signal is measured, as different gain functions may be employed for different CGM use periods (e.g., 3-21 hours, 12-45 hours, 40-167 hours, or the like). For example, processor 710 (or processor 720) may be employed to compute the ratio and other cross terms used in a stored gain function, and to compute a compensated glucose value using equation $G_{Comp}=Signal_{Raw}*Gain*(1/(1+Gain\ Function))$. This may alternatively be viewed as adjusting the system gain (Gain) based on the gain function, and then using the adjusted gain function to compute the compensated glucose value (e.g., concentration).

In Block 1010, the compensated glucose value is communicated to the user of the CGM device. For example, display 117 (FIG. 7A) or display 722 (FIG. 7B) may display the glucose value. Alternatively, the glucose value may be used as part of a trend line, graph or image. In some embodiments, the compensated glucose value may not be displayed until much later in the future, and/or until a user requests to have the glucose value displayed.

In some embodiments, other analytes may be measured using continuous monitoring in accordance with embodiments provided herein. For example, concentration of cholesterol, lactate, uric acid, alcohol, or the like may be detected using an analyte or other biosensor, a point-of-interest analyte signal, previously-measured analyte signals and one or more suitable gain functions.

Figure 11:
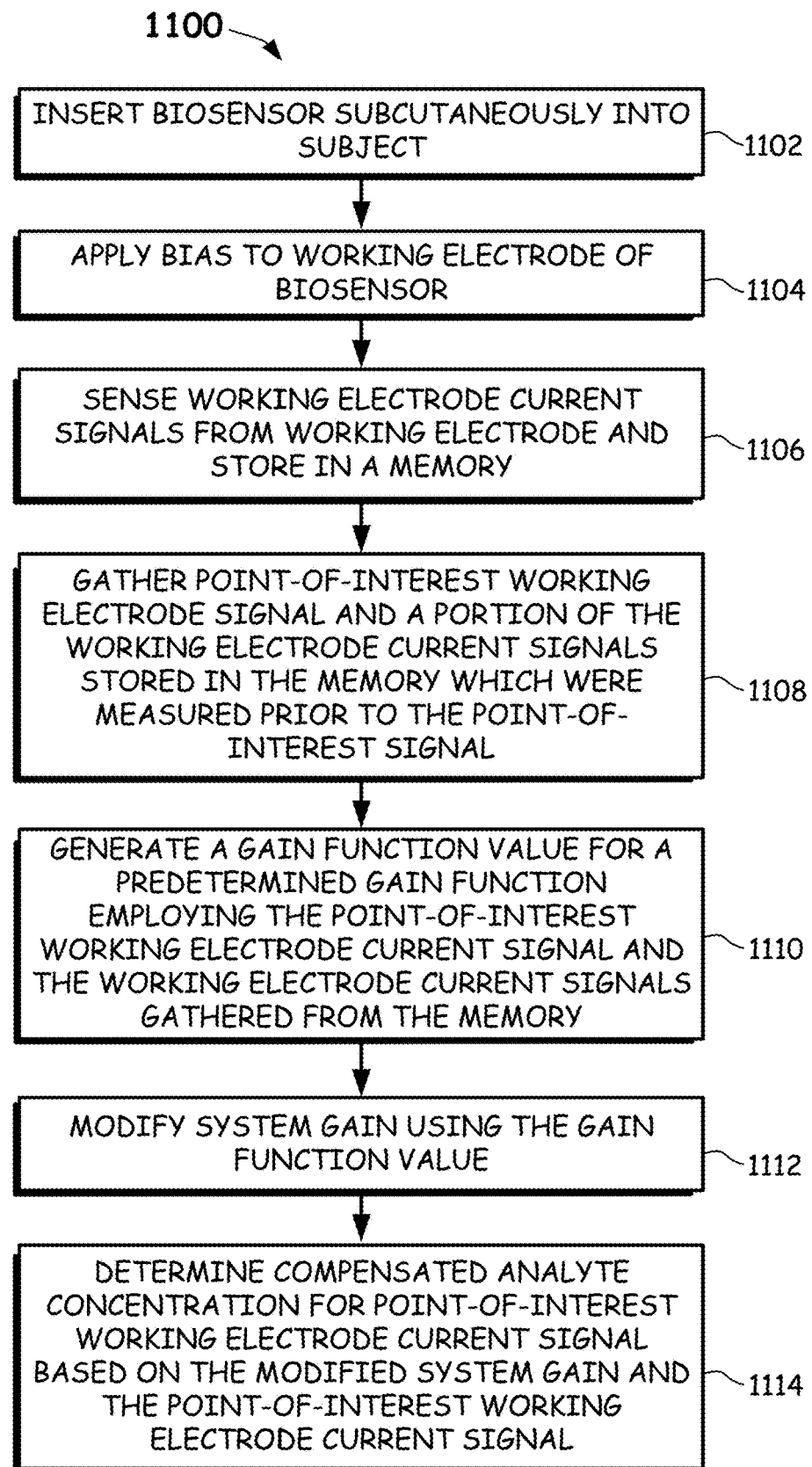
FIG. 11 illustrates an example method of determining analyte concentrations during continuous monitoring measurements with a biosensor inserted subcutaneously into a subject in accordance with embodiments provided herein.

FIG. 11 illustrates an example method 1100 of determining analyte concentrations during continuous monitoring measurements with a biosensor inserted subcutaneously into a subject in accordance with embodiments provided herein. With reference to FIG. 11, the method 1100 of determining analyte concentrations during continuous monitoring measurements includes inserting a biosensor subcutaneously into a subject (Block 1102). In some embodiments, the biosensor may include a counter electrode, a reference electrode and a working electrode having a chemical composition configured to oxidize a point-of-interest analyte. For example, CGM sensor 704 or another analyte sensor may be inserted into a user. A bias voltage such as a constant voltage may be applied to the working electrode (Block 1104) so as to generate a continuous current flow from the working electrode. In Block 1106, working electrode current signals from the working electrode may be sensed and stored into a memory (e.g., memory 712 of CGM device 700 or 750, or a memory of another continuous analyte monitoring device). For example, working electrode current signals may be periodically sensed (e.g., sampled) and stored.

In Block 1108, a point-of-interest working electrode current signal and a portion of the working electrode current signals stored in the memory which were measured prior to the point-of-interest working electrode current signal may be gathered (e.g., read from the memory). A gain function value may then be generated from a predetermined gain function employing the point-of-interest working electrode current signal and the portion of the working electrode current signals gathered from the memory (Block 1110). For example, ratios and/or differences based on the point-of-interest working electrode current signal and the portion of the working electrode current signals gathered from the memory may be employed within the predetermined gain function.

A system gain may be modified using the gain function value generated from the predetermined gain function (Block 1112). For glucose, the system gain may be based on an in-situ calibration using a BGM glucose value. System gains for other analytes may be similarly determined based on a reference analyte concentration and a working electrode current signal (e.g., $Gain=A_{Calb}/(Iw)$ or $A_{Calb}/(Iw-Ib)$, where $A_{Calb}$ is a reference analyte value). In Block 1114, compensated analyte concentration ($A_{Comp}$) for the point-of-interest working electrode current signal may be determined based on the modified system gain and the point-of-interest working electrode current signal:

$$A_{Comp}=Signal_{Raw}*Gain*(1/(1+Gain\ Function)), \quad (25)$$

where $Gain*(1/(1+Gain\ Function))$ represents the modified system gain.

Example analytes include glucose, cholesterol, lactate, uric acid, alcohol, or the like. In some embodiments, background current signals may be stored with working electrode signals in the memory, and used to remove signals from interference substances such as Vitamin C, acetaminophen, etc.

In yet another embodiment, a continuous analyte monitoring (CAM) device may include a wearable portion having a biosensor configured to be subcutaneously inserted into a subject. The biosensor may include a counter electrode, a reference electrode and a working electrode having a chemical composition configured to oxidize a point-of-interest analyte and to produce analyte (e.g., glucose) signals from interstitial fluid. The wearable portion may also have a processor, a memory coupled to the processor, and transmitter circuitry coupled to the processor (as shown, for example, in FIG. 7A for CGM device 700). The memory may include a predetermined gain function based on a point-of-interest analyte signal and analyte signals measured prior to the point-of-interest analyte signal. Additionally, the memory may include computer program code stored therein that, when executed by the processor, causes the CAM device to (a) apply a constant voltage to the working electrode having the chemical composition so as to generate a continuous current flow from the working electrode; (b) sense and store working electrode current signals from the working electrode into the memory; (c) gather a point-of-interest working electrode current signal and a portion of the working electrode current signals stored in the memory which were measured prior to the point-of-interest working electrode current signal; (d) generate a gain function value from the gain function employing the point-of-interest working electrode current signal and the portion of the working electrode current signals gathered from the memory; (e) modify a system gain using the gain function value generated from the predetermined gain function; and (f) determine an analyte concentration for the point-of-interest working electrode current signal based on the modified system gain and the point-of-interest working electrode current signal. For example, in some embodiments, analyte concentration using a modified system gain may be calculated using equation (25) above.

Figure 12:
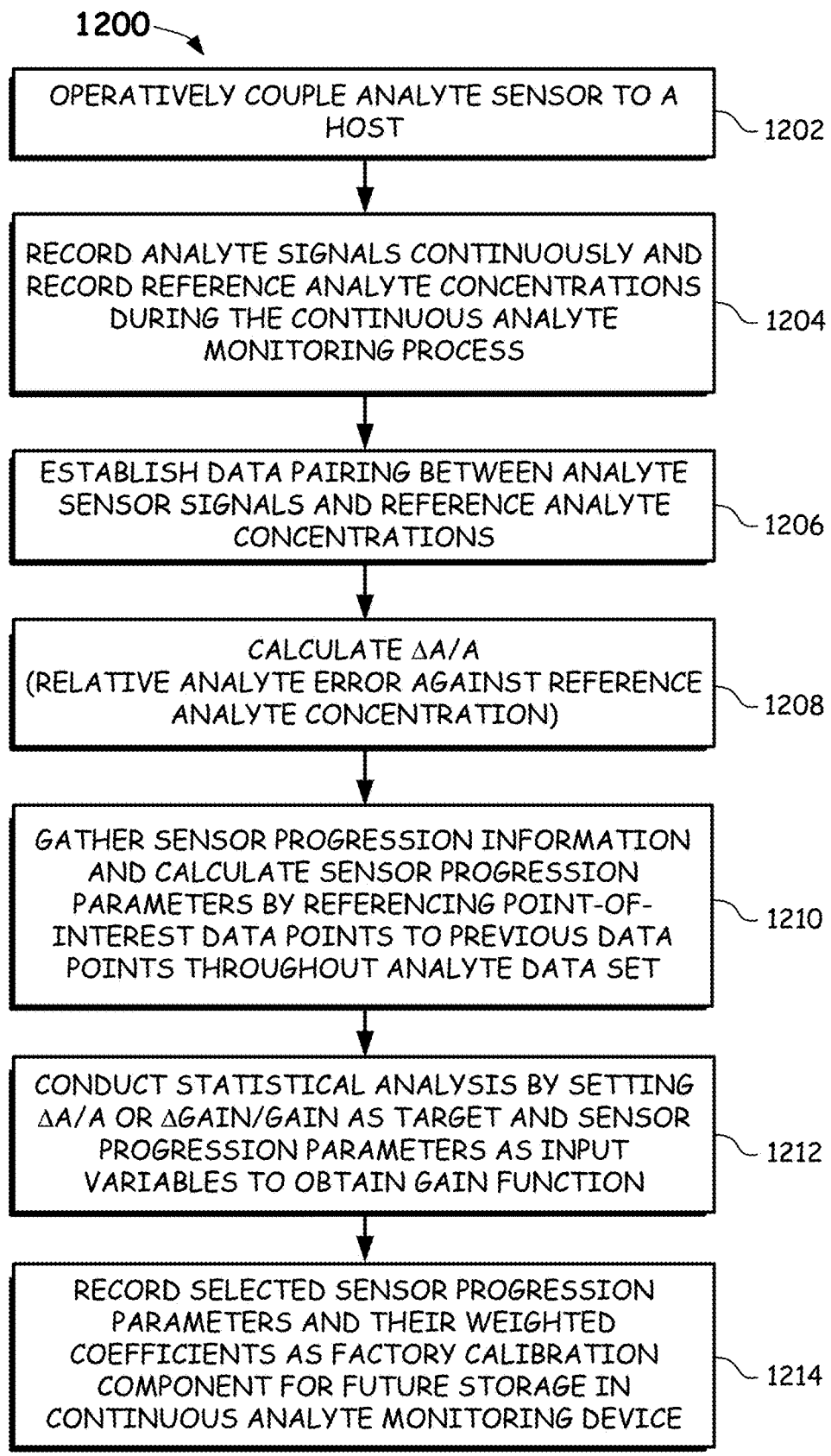
FIG. 12 illustrates another example method of making a continuous analyte monitoring device in accordance with embodiments provided herein.

FIG. 12 illustrates another example method 1200 of making a continuous analyte monitoring device in accordance with embodiments provided herein. With reference to FIG. 12, in Block 1202, an analyte sensor is operatively coupled to a host. For example, an analyte sensor may be inserted through the skin of the host so that the analyte sensor contacts an interstitial fluid region. Example analytes that may be detected include glucose, cholesterol, lactate, uric acid, alcohol, or the like.

In Block 1204, the analyte sensor is employed to record analyte signals continuously, such as at a regular sampling rate. For example, analyte signals may be recorded (e.g., sensed, measured, sampled and/or stored) every 1, 2, 3, 5, 10 minutes or at any other increment. In some embodiments, analyte signals may be collected as part of a clinical study using multiple analyte sensors and multiple hosts. Reference analyte concentrations also may be recorded (e.g., periodically during the continuous analyte monitoring process). For example, a reference analyte device, such as a blood glucose meter, may be employed to record a reference analyte concentration. Reference analyte concentrations may be recorded at any suitable time increment such as every hour, day, every other day, or the like.

In Block 1206, analyte sensor signals are paired with reference analyte concentrations. For example, analyte signals measured after a reference analyte concentration is recorded may be paired with the recorded reference analyte concentration until another reference analyte concentration is recorded. Other pairings may be used.

Figure 13:
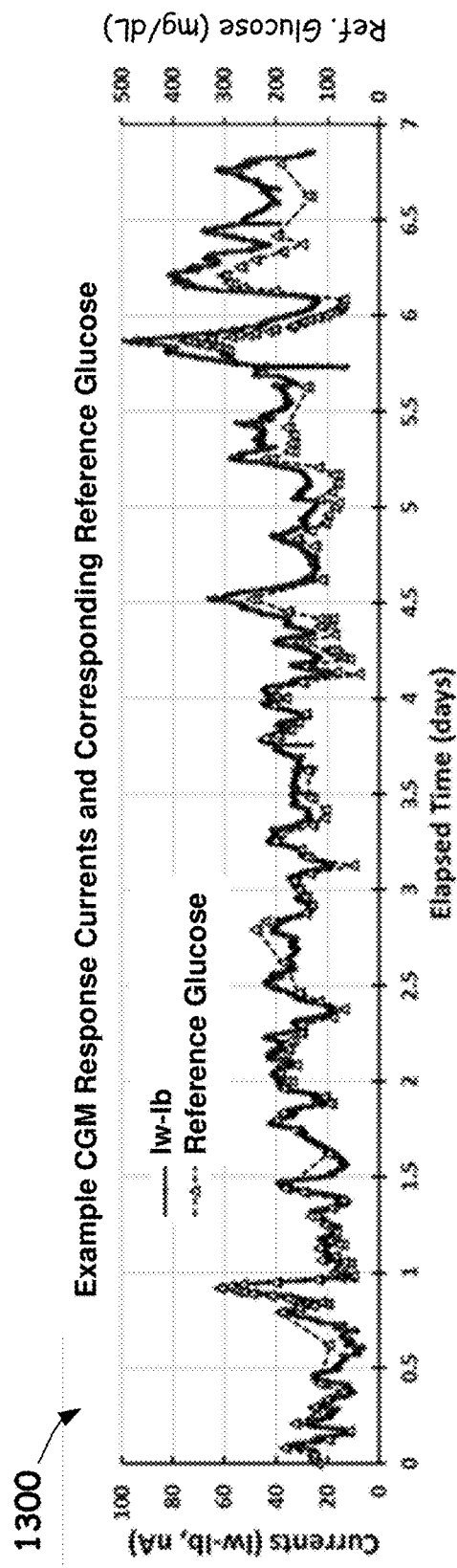
FIG. 13 is a graph of example CGM response currents paired with reference values from a blood glucose meter in accordance with embodiments provided herein.

FIG. 13 is a graph 1300 of example CGM response currents, such as Iw–Ib, paired with reference glucose values from a blood glucose meter (e.g., a Contour Next One® blood glucose meter) in accordance with embodiments provided herein. As shown in FIG. 13, Iw–Ib tracks the reference glucose values. In some embodiments, glucose signals measured 3-5 minutes before a new reference glucose value is measured are paired with the new reference glucose value, rather than with the previously-recorded reference glucose value.

Figure 14:
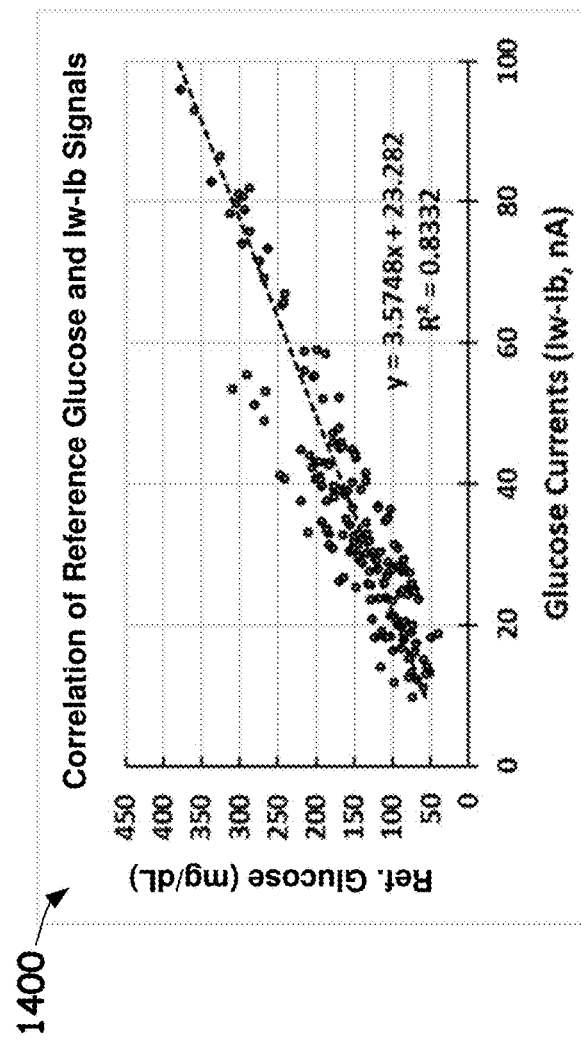
FIG. 14 is a graph of example reference glucose values versus glucose currents during a CGM process in accordance with embodiments provided herein.

FIG. 14 is a graph 1400 of example reference glucose values versus glucose currents, such as Iw–Ib, during a CGM process in accordance with embodiments provided herein. As shown in FIG. 14, glucose current signals accurately track reference glucose values, with an $R^2$ value of 0.83.

In Block 1208, the relative analyte error $\Delta A/A$ is computed. For example, analyte error may be equated to signal error $\Delta Signal/Signal$ and computed using equation (23) above.

In Block 1210, sensor progression information is gathered and used to calculate sensor progression parameters by referencing point-of-interest analyte data points to previously-measured analyte data points throughout the data set. For example, sensor progression parameters may be calculated for each point-of-interest analyte signal by computing ratios, differences, or other relationships between the point-of-interest analyte signal and analyte signals measured prior to the point-of-interest analyte signal.

In Block 1212, statistical analysis is conducted by setting at least one of relative analyte error referenced against reference analyte concentration and relative gain error referenced against reference gain as a target for the statistical analysis and sensor progression parameters as input variables so as to obtain a gain function. In some embodiments, the statistical analysis may include multivariate regression. Other statistical analysis methods may be used. As stated, tens, hundreds or thousands of sensor progression parameters may be employed to obtain a gain function.

In Block 1214, the obtained gain function is recorded as a factory calibration component for storage in a continuous analyte monitoring device. The gain function includes selected sensor progression parameters and their weighted coefficients. As described previously with reference to FIG. 2, more than one gain function may be determined for an analyte data set (e.g., 2, 3, 4 or more). In some embodiments, the gain function may be stored in a CGM device, such as in memory 712 of CGM device 700, or in another continuous analyte monitoring device. Gain functions may be based on electrochemical signals, optical signals or the like.

The foregoing description discloses only example embodiments. Modifications of the above-disclosed apparatus and methods which fall within the scope of this disclosure will be readily apparent to those of ordinary skill in the art.

APPENDIX

The below listed gain functions, coefficients, sensor progression parameters, and/or cross terms are merely examples. Other gain functions, coefficients, sensor progression parameters, and/or cross terms may be employed.

Gain Function 1 (3-20 Hours)
Gain Function 1=3.091118+1.471262*w27min−0.984106*w2h−2.665682*b3min−2.254352*b18min+2.314656*b1h−0.0149674*w6mG−0.0227495*w24mG+1.117723*w27mSS1+0.951549*w3hSS1+0.0020214*w3hGSS1+0.536988*w3m2h−0.97541*w9m2h+0.326197*w15m1h+0.699317*w24m2h−0.397502*w27m2h+0.0287526*b3mG−0.01240012*b6mG−0.43543*b3hSS1−0.0025204*b30mGSS1−0.841776*w27mb6mSS1−1.268666*w3hb9mSS1 . . .

Gain Function 2 (12-45 Hours)
Gain Function 2=6.333784+2.7006532*w9min−0.4503101*b1h−0.0004858*w9mGSS1+9.35e−5*w12hGSS1+0.0930561*w3m3h−0.0721993*w3m12h+0.292186*w9m1h−0.2503538*w12m2h−0.231265*w21m2h+0.508004*w24m2h−0.2291636*w30m1h−0.0584004*w30m3h+0.0409812*w30m4h−0.0041765*b6mG+0.0039682*b12hG−0.1346056*b6hSS1+0.0010892*b1hGSS1+0.0009736*b10hGSS1+0.1471952*w8hb4hSS1−0.0364746*w12hb4hSS1 . . .

Gain Function 3 (40-167 Hours)
Gain Function 3=0.979878−0.637773*w9min+0.0001337*w2hGSS1+0.0001573*w12hGSS1+0.167157*w3m3h−0.325834*w3m12h+0.311399*w6m12h+0.378304*w12m1h−0.308914*w12m3h−0.022367*w18m10h−0.377033*w27m1h+0.167712*w27m3h−0.390158*b15mSS1+0.356742*b8hSS1−0.0008352*b9mGSS1+0.0008576*b4hGSS1−0.204995*w3mb2h−0.59261*w6mb1h+0.0020452*Gw12hb12h−0.296086*w12hb12mSS1+0.289866*w12hb12hSS1 . . .

Gain Function 1 Sensor Progression Parameters and Cross Terms
$Gain_i = BGM_{cal-i}/(Iw-Ib)_{cal-i}$, at i in-situ calibration point where i=1, 2, . . . 10, etc.

$S/S1 = Gain_i/Gain_1$, the ratio of an individual $Gain_i$ to $Gain_1 = BGM_{cal-1}/(Iw-Ib)_{cal-1}$ $G_{raw} = 0.85*(Iw-Ib)t*Gain_i$, if $Gain_i > 12$; elseif $Gain_i > 8$, $0.9*(Iw-Ib)t*Gain_i$; else $(Iw-Ib)t*Gain_i$ $w27min = (Iw-Ib)_t/(Iw-Ib)_{t-27min}$, ratio of Iw-Ib at time t to Iw-Ib at time of t-27min $w2h = (Iw-Ib)_t/(Iw-Ib)_{t-2hour}$, ratio of Iw-Ib at time t to Iw-Ib at time of t-2hour $b3min = Ib_t/Ib_{t-3min}$, ratio of Ib at time t to Ib at time of t-3min $b18min = Ib_t/Ib_{t-18min}$ $b1h = Ib_t/Ib_{t-1hour}$ $w6mG = G_{raw}*(Iw-Ib)_t/(Iw-Ib)_{t-6min}$ $w24mG = G_{raw}*(Iw-Ib)_t/(Iw-Ib)_{t-24min}$ $w27mSS1 = (S/S1)*(Iw-Ib)_t/(Iw-Ib)_{t-27min}$ $w3hSS1 = (S/S1)*(Iw-Ib)_t/(Iw-Ib)_{t-3hour}$ $w3hGSS1 = G_{raw}*(S/S1)*(Iw-Ib)_t/(Iw-Ib)_{t-3hour}$ $w3m2h = w\_3min/w\_2h = [(Iw-Ib)_t/(Iw-Ib)_{t-3min}]/[(Iw-Ib)_t/(Iw-Ib)_{t-2hour}] = (Iw-Ib)_{t-2hour}/(Iw-Ib)_{t-3min}$ $w9m2h = w\_9min/w\_2h = [(Iw-Ib)_t/(Iw-Ib)_{t-9min}]/[(Iw-Ib)_t/(Iw-Ib)_{t-2hour}] = (Iw-Ib)_{t-2hour}/(Iw-Ib)_{t-9min}$ $w15m1h = w\_15min/w\_1h = [(Iw-Ib)_t/(Iw-Ib)_{t-15min}]/[(Iw-Ib)_t/(Iw-Ib)_{t-1hour}] = (Iw-Ib)_{t-1hour}/(Iw-Ib)_{t-15min}$ $w24m2h = w\_24min/w\_2h = [(Iw-Ib)_t/(Iw-Ib)_{t-24min}]/[(Iw-Ib)_t/(Iw-Ib)_{t-2hour}] = (Iw-Ib)_{t-2hour}/(Iw-Ib)_{t-24min}$ $w27m2h = w\_27min/w\_2h = [(Iw-Ib)_t/(Iw-Ib)_{t-27min}]/[(Iw-Ib)_t/(Iw-Ib)_{t-2hour}] = (Iw-Ib)_{t-2hour}/(Iw-Ib)_{t-27min}$ $b3mG = G_{raw}*Ib_t/Ib_{t-3min}$ $b6mG = G_{raw}*Ib_t/Ib_{t-6min}$ $b3hSS1 = (S/S1)*Ib_t/Ib_{t-3hour}$ $b30mGSS1 = G_{raw}*(S/S1)*Ib_t/Ib_{t-30min}$ $w27mb6mSS1 = (S/S1)*w\_27min/b\_6min = (S/S1)*[(Iw-Ib)_t/(Iw-Ib)_{t-27min}]/[Ib_t/Ib_{t-6min}]$ $w3hb9mSS1 = (S/S1)*w\_3h/b\_9min = (S/S1)*[(Iw-Ib)_t/(Iw-Ib)_{t-3hour}]/[Ib_t/Ib_{t-9min}]$ Gain Function 2 Sensor Progression Parameters and Cross Terms $Gain_i = BGM_{cal-i}/(Iw-Ib)_{cal-i}$, at i in-situ calibration point where i=1, 2, . . . 10, etc.

$S/S1 = Gain_i/Gain_1$, the ratio of an individual $Gain_i$ to $Gain1 = BGM_{cal-1}/(Iw-Ib)_{cal-1}$ $G_{raw} = 0.85*(Iw-Ib)_t*Gain_i$, if $Gaini > 12$; elseif $Gain_i > 8$, $0.9*(Iw-Ib)t*Gain_i$; else $(Iw-Ib)t*Gain_i$ $w9min = (Iw-Ib)_t/(Iw-Ib)_{t-9min}$, ratio of Iw-Ib at time t to Iw-Ib at time of t-9min $b1h = Ib_t/Ib_{t-1hour}$, ratio of Ib at time t to Ib at time of t-1hour $w9mGSS1 = G_{raw}*(S/S1)*(Iw-Ib)_t/(Iw-Ib)_{t-9min}$ $w12hGSS1 = G_{raw}*(S/S1)*(Iw-Ib)_t/(Iw-Ib)_{t-12hour}$ $w3m3h = w\_3min/w\_3h = [(Iw-Ib)_t/(Iw-Ib)_{t-3min}]/[(Iw-Ib)_t/(Iw-Ib)_{t-3hour}] = (Iw-Ib)_{t-3hour}/(Iw-Ib)_{t-3min}$ $w3m12h = w\_3min/w\_12h = [(Iw-Ib)_t/(Iw-Ib)_{t-3min}]/[(Iw-Ib)_t/(Iw-Ib)_{t-12hour}] = (Iw-Ib)_{t-12hour}/(Iw-Ib)_{t-3min}$ $w9m1h = w\_9min/w\_1h = [(Iw-Ib)_t/(Iw-Ib)_{t-9min}]/[(Iw-Ib)_t/(Iw-Ib)_{t-1hour}] = (Iw-Ib)_{t-1hour}/(Iw-Ib)_{t-9min}$ $w12m2h = w\_12min/w\_2h = [(Iw-Ib)_t/(Iw-Ib)_{t-12min}]/[(Iw-Ib)_t/(Iw-Ib)_{t-2hour}] = (Iw-Ib)_{t-2hour}/(Iw-Ib)_{t-12min}$ $w21m2h = w\_21min/w\_2h = [(Iw-Ib)_t/(Iw-Ib)_{t-21min}]/[(Iw-Ib)_t/(Iw-Ib)_{t-2hour}] = (Iw-Ib)_{t-2hour}/(Iw-Ib)_{t-21min}$ $w24m2h = w\_24min/w\_2h = [(Iw-Ib)_t/(Iw-Ib)_{t-24min}]/[(Iw-Ib)_t/(Iw-Ib)_{t-2hour}] = (Iw-Ib)_{t-2hour}/(Iw-Ib)_{t-24min}$ $w30m1h = w\_30min/w\_1h = [(Iw-Ib)_t/(Iw-Ib)_{t-30min}]/[(Iw-Ib)_t/(Iw-Ib)_{t-1hour}] = (Iw-Ib)_{t-1hour}/(Iw-Ib)_{t-30min}$ $w30m3h = w\_30min/w\_3h = [(Iw-Ib)_t/(Iw-Ib)_{t-30min}]/[(Iw-Ib)_t/(Iw-Ib)_{t-3hour}] = (Iw-Ib)_{t-3hour}/(Iw-Ib)_{t-30min}$ $w30m4h = w\_30min/w\_4h = [(Iw-Ib)_t/(Iw-Ib)_{t-30min}]/[(Iw-Ib)_t/(Iw-Ib)_{t-4hour}] = (Iw-Ib)_{t-4hour}/(Iw-Ib)_{t-30min}$ $b6mG = G_{raw}*Ib_t/Ib_{t-6min}$ $b12hG = G_{raw}*Ib_t/Ib_{t-12hour}$ $b6hSS1 = (S/S1)*Ib_t/Ib_{t-6hour}$ $b1hGSS1 = G_{raw}*(S/S1)*Ib_t/Ib_{t-1hour}$ $b10hGSS1 = G_{raw}*(S/S1)*Ib_t/Ib_{t-10hour}$ $w8hb4hSS1 = (S/S1)*w\_8h/b\_4h = (S/S1)*[(Iw-Ib)_t/(Iw-Ib)_{t-8hour}]/[Ib_t/Ib_{t-4hour}]$ $w12hb4hSS1 = (S/S1)*w\_12h/b\_4h = (S/S1)*[(Iw-Ib)_t/(Iw-Ib)_{t-12hour}]/[Ib_t/Ib_{t-4hour}]$ Gain Function 3 Sensor Progression Parameters and Cross Terms $Gain_i = BGM_{cal-i}/(Iw-Ib)_{cal-i}$, at i in-situ calibration point where i=1, 2, . . . 10, etc.

$S/S1 = Gain_i/Gain_1$, the ratio of an individual $Gain_i$ to $Gain_1 = BGM_{cal-1}/(Iw-Ib)_{cal-1}$ $G_{raw} = 0.85*(Iw-Ib)_t*Gain_i$, if $Gain_i > 12$; elseif $Gain_i > 8$, $0.9*(Iw-Ib)_t*Gain_i$; else $(Iw-Ib)t*Gain_i$ $w9min = (Iw-Ib)_t/(Iw-Ib)_{t-9min}$, ratio of Iw-Ib at time t to Iw-Ib at time of t-9min $w2hGSS1 = G_{raw}*(S/S1)*(Iw-Ib)_t/(Iw-Ib)_{t-2hour}$ $w12hGSS1 = G_{raw}*(S/S1)*(Iw-Ib)_t/(Iw-Ib)_{t-12hour}$ $w3m3h = w\_3min/w\_3h = [(Iw-Ib)_t/(Iw-Ib)_{t-3min}]/[(Iw-Ib)_t/(Iw-Ib)_{t-3hour}] = (Iw-Ib)_{t-3hour}/(Iw-Ib)_{t-3min}$ $w3m12h = w\_3min/w\_12h = [(Iw-Ib)_t/(Iw-Ib)_{t-3min}]/[(Iw-Ib)_t/(Iw-Ib)_{t-12hour}] = (Iw-Ib)_{t-12hour}/(Iw-Ib)_{t-3min}$ $w6m12h = w\_6min/w\_12h = [(Iw-Ib)_t/(Iw-Ib)_{t-6min}]/[(Iw-Ib)_t/(Iw-Ib)_{t-12hour}] = (Iw-Ib)_{t-12hour}/(Iw-Ib)_{t-6min}$ $w12m1h = w\_12min/w\_1h = [(Iw-Ib)_t/(Iw-Ib)_{t-12min}]/[(Iw-Ib)_t/(Iw-Ib)_{t-1hour}] = (Iw-Ib)_{t-1hour}/(Iw-Ib)_{t-12min}$ $w12m3h = w\_12min/w\_3h = [(Iw-Ib)_t/(Iw-Ib)_{t-12min}]/[(Iw-Ib)_t/(Iw-Ib)_{t-3hour}] = (Iw-Ib)_{t-3hour}/(Iw-Ib)_{t-12min}$ $w18m10h = w\_18min/w\_10h = [(Iw-Ib)_t/(Iw-Ib)_{t-18min}]/[(Iw-Ib)_t/(Iw-Ib)_{t-10hour}] = (Iw-Ib)_{t-10hour}/(Iw-Ib)_{t-18min}$ $w27m1h = w\_27min/w\_1h = [(Iw-Ib)_t/(Iw-Ib)_{t-27min}]/[(Iw-Ib)_t/(Iw-Ib)_{t-1hour}] = (Iw-Ib)_{t-1hour}/(Iw-Ib)_{t-27min}$ $w27m3h = w\_27min/w\_3h = [(Iw-Ib)_t/(Iw-Ib)_{t-27min}]/[(Iw-Ib)_t/(Iw-Ib)_{t-3hour}] = (Iw-Ib)_{t-3hour}/(Iw-Ib)_{t-27min}$ $b15mSS1 = (S/S1)*Ib_t/Ib_{t-15min}$ $b8hSS1 = (S/S1)*Ib_t/Ib_{t-8hour}$ $b9mGSS1 = G_{raw}*(S/S1)*Ib_t/Ib_{t-9min}$ $b4hGSS1 = G_{raw}*(S/S1)*Ib_t/Ib_{t-4hour}$ $w3mb2h = w\_3min/b\_2h = [(Iw-Ib)_t/(Iw-Ib)_{t-3min}]/[Ib_t/Ib_{t-2hour}]$ $w6mb1h = w\_6min/b\_1h = [(Iw-Ib)_t/(Iw-Ib)_{t-6min}]/[Ib_t/Ib_{t-1hour}]$ $Gw12hb12h = G_{raw}*w\_12h/b\_12h = G_{raw}*[(Iw-Ib)_t/(Iw-Ib)_{t-12hour}]/[Ib_t/Ib_{t-12hour}]$ $w12hb12mSS1 = (S/S1)*w\_12h/b\_12min = (S/S1)*[(Iw-Ib)_t/(Iw-Ib)_{t-12hour}]/[Ib_t/Ib_{t-12min}]$ $w12hb12hSS1 = (S/S1)*w\_12h/b\_12h = (S/S1)*[(Iw-Ib)_t/(Iw-Ib)_{t-12hour}]/[Ib_t/Ib_{t-12hour}]$

What is claimed is:

1. A method of determining concentrations of an analyte during continuous monitoring measurements comprising:
inserting a biosensor subcutaneously into a subject, the biosensor including a counter electrode, a reference electrode, a background electrode, and a working electrode having a chemical composition configured to oxidize a point-of-interest analyte;
applying a constant voltage to the working electrode having the chemical composition to generate a continuous current flow from the working electrode;
sensing and storing working electrode current signals from the working electrode into a memory;
sensing and storing background electrode current signals from the background electrode into the memory;

gathering a point-of-interest working electrode current signal and a portion of the working electrode current signals stored in the memory which were measured prior to the point-of-interest working electrode current signal;

gathering a point-of-interest background electrode current signal and a portion of the background electrode current signals stored in the memory which were measured prior to the point-of-interest background electrode current signal;

generating a gain function value from a predetermined gain function employing the point-of-interest working electrode current signal, the point-of-interest background electrode current signal, the portion of the working electrode current signals gathered from the memory, and the portion of the background electrode current signals gathered from the memory;

modifying a system gain based on the gain function value generated from the predetermined gain function; and determining an analyte concentration for the point-of-interest working electrode current signal by applying the system gain to the point-of-interest working electrode current signal; and communicating the analyte concentration to a user.

2. The method of claim 1 wherein the analyte is glucose.

3. The method of claim 1 wherein recording and storing current signals from the working electrode into the memory occurs periodically.

4. The method of claim 1 wherein generating the gain function value comprises determining ratios based on the point-of-interest working electrode current signal and the portion of the working electrode current signals gathered from the memory.

5. The method of claim 1 wherein generating the gain function value comprises determining differences based on the point-of-interest working electrode current signal and the portion of the working electrode current signals gathered from the memory.

6. The method of claim 1, wherein generating the gain function value comprises determining a difference between the point-of-interest working electrode current signal and the point-of-interest background electrode current signal gathered from the memory.

7. The method of claim 6 wherein the gain function value is generated from a predetermined gain function employing the point-of-interest working electrode current signal, the portion of the working electrode current signals gathered from the memory, and the portion of the background electrode current signals stored in the memory.

8. The method of claim 1 wherein the predetermined gain function is factory determined using multi-variate regression and stored in the memory.

9. The method of claim 1 wherein the gain function value is based on a working electrode signal measured at least one hour before the point-of-interest working electrode signal.

10. The method of claim 1 wherein the gain function value is based on a working electrode signal measured between 6 and 12 hours before the point-of-interest working electrode signal.

11. The method of claim 1 wherein the predetermined gain function employs ratios of point-of-interest working electrode signals and previously-measured working electrode signals.

12. A continuous analyte monitoring (CAM) device comprising:

a wearable portion having:
   a biosensor configured to be subcutaneously inserted into a subject, the biosensor including a counter electrode, a reference electrode, a background electrode, and a working electrode having a chemical composition configured to oxidize a point-of-interest analyte and to produce analyte signals from interstitial fluid;
   a processor;
   a memory coupled to the processor; and
   transmitter circuitry coupled to the processor;
   wherein the memory includes a predetermined gain function based on a point-of-interest analyte signal and analyte signals measured prior to the point-of-interest analyte signal;
   wherein the memory includes computer program code stored therein that, when executed by the processor, causes the CAM device to:
      apply a constant voltage to the working electrode having the chemical composition to generate a continuous current flow from the working electrode;
      sense and store working electrode current signals from the working electrode into the memory;
      sense and store background electrode current signals from the background electrode into the memory;
      gather a point-of-interest working electrode current signal and a portion of the working electrode current signals stored in the memory which were measured prior to the point-of-interest working electrode current signal;
      gather a point-of-interest background electrode current signal and a portion of the background electrode current signals stored in the memory which were measured prior to the point-of-interest background electrode current signal
      generate a gain function value from the predetermined gain function employing the point-of-interest working electrode current signal, the point-of-interest background electrode current signal, the portion of the working electrode current signals gathered from the memory, and the portion of the background electrode current signals gathered from the memory;
      modify a system gain using the gain function value generated from the predetermined gain function; and
      determine an analyte concentration for the point-of-interest working electrode current signal by applying the system gain to the point-of-interest working electrode current signal; and
      communicate the analyte concentration to a user.

13. The CAM device of claim 12 wherein the predetermined gain function is factory determined using multi-variate regression and stored in the memory.

14. The CAM device of claim 12 wherein the gain function value is based on a working electrode signal measured at least one hour before the point-of-interest working electrode signal.

15. The CAM device of claim 12 wherein the gain function value is based on a working electrode signal measured between 6 and 12 hours before the point-of-interest working electrode signal.

16. The CAM device of claim 12 wherein the predetermined gain function employs ratios of point-of-interest working electrode signals and previously-measured working electrode signals.

17. A method of making a continuous analyte monitoring device, comprising:

operatively coupling an analyte sensor with a host;
continuously recording analyte signals from the analyte sensor during a continuous analyte monitoring process;

recording reference analyte concentrations from a reference analyte electrode at discrete time increments during the continuous analyte monitoring process;

establishing a data pairing between the analyte signals and the reference analyte concentrations;

calculating a gain curve as a ratio of the reference analyte concentrations to the analyte signals for each data pairing;

calculating sensor progression parameters from a point-of-interest analyte signal and a plurality of previously-measured analyte signals;

applying multivariate regression to the gain curve and the sensor progression parameters to determine a gain function; and recording the gain function with the sensor progression parameters and corresponding weighted coefficients as a factory calibration component for storage in the continuous analyte monitoring device.

18. The method of claim 17 wherein at least one sensor progression parameter is based on an analyte signal measured at least one hour before the point-of-interest analyte signal.

19. The method of claim 17 wherein at least one sensor progression parameter is based on an analyte signal measured between 6 and 12 hours before the point-of-interest analyte signal.

20. The method of claim 17 wherein the gain function employs ratios of the point-of-interest analyte signal and the plurality of previously-measured analyte signals.

* * * * *